United States Patent
Dees, Jr. et al.

(10) Patent No.: US 9,808,348 B2
(45) Date of Patent: Nov. 7, 2017

(54) IMPLANTS WITH TRANSITION SURFACES AND RELATED PROCESSES

(75) Inventors: Roger Ryan Dees, Jr., Senatobia, MS (US); Jason Jordan, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 1461 days.

(21) Appl. No.: 12/944,124

(22) Filed: Nov. 11, 2010

(65) Prior Publication Data

US 2011/0060340 A1    Mar. 10, 2011

Related U.S. Application Data

(62) Division of application No. 11/850,178, filed on Sep. 5, 2007.

(Continued)

(51) Int. Cl.
  *A61F 2/38*     (2006.01)
  *A61B 17/15*    (2006.01)
  (Continued)

(52) U.S. Cl.
  CPC .............. *A61F 2/38* (2013.01); *A61B 17/155* (2013.01); *A61F 2/3859* (2013.01);
  (Continued)

(58) Field of Classification Search
  CPC ....................................................... A61F 2/38
  (Continued)

(56) References Cited

U.S. PATENT DOCUMENTS

| 4,178,641 A | 12/1979 | Grundei et al. |
| 4,524,766 A | 6/1985 | Petersen |

(Continued)

FOREIGN PATENT DOCUMENTS

| AU | 6624686 A | 6/1987 |
| DE | 2703059 | 7/1978 |

(Continued)

OTHER PUBLICATIONS

Office Action for U.S. Appl. No. 11/850,178, dated Oct. 25, 2011, 28 pages.

(Continued)

*Primary Examiner* — Thomas J Sweet
*Assistant Examiner* — Melissa Hoban
(74) *Attorney, Agent, or Firm* — Fish & Richardson P.C.

(57) ABSTRACT

Implants, and processes for installing them, which replace the medial condyle and portions of the patellofemoral channel but preferably not portions of the lateral condyle that articulate relative to the tibia. Processes are provided which allow proper location and orientation of an anterior resection and a distal resection on the femur, which make use of a transition point which can be designated on the bone, for navigating proper positioning of such implants. Proper positioning of the implant relative to the femur for insuring a smooth transition between lateral portions of the implant and the lateral condyle is thus reduced to determining proper medial/lateral location of the implant on the anterior and distal resections. Such implants and processes can allow, among other things, for controlled location and orientation of an implant on the bone which saves lateral compartment bone, which eliminates the need to sacrifice the anterior and posterior cruciate ligaments, and which is adapted for minimally invasive surgery with its attendant benefits.

6 Claims, 46 Drawing Sheets

Related U.S. Application Data

(60) Provisional application No. 60/828,158, filed on Oct. 4, 2006, provisional application No. 60/824,696, filed on Sep. 6, 2006, provisional application No. 60/825,533, filed on Sep. 13, 2006.

(51) Int. Cl.
   *A61B 17/17* (2006.01)
   *A61F 2/30* (2006.01)

(52) U.S. Cl.
   CPC ......... *A61B 17/1764* (2013.01); *A61F 2/3877* (2013.01); *A61F 2002/30001* (2013.01); *A61F 2002/3895* (2013.01)

(58) Field of Classification Search
   USPC ...................................................... 623/20.3
   See application file for complete search history.

(56) References Cited

U.S. PATENT DOCUMENTS

| | | | |
|---|---|---|---|
| 4,907,578 A | 3/1990 | Peterson | |
| 5,092,895 A | 3/1992 | Albrektsson et al. | |
| 5,314,482 A | 5/1994 | Goodfellow et al. | |
| 5,336,266 A | 8/1994 | Caspari et al. | |
| 5,474,559 A | 12/1995 | Bertin et al. | |
| 5,486,180 A | 1/1996 | Dietz et al. | |
| 5,520,695 A | 5/1996 | Luckman | |
| 5,676,668 A | 10/1997 | McCue et al. | |
| 5,702,459 A | 12/1997 | Hummer et al. | |
| 5,702,467 A | 12/1997 | Gabriel et al. | |
| 5,738,686 A | 4/1998 | Kubein-Meesenburg et al. | |
| 6,074,425 A | 6/2000 | Pappas | |
| 6,077,270 A | 6/2000 | Katz | |
| 6,325,828 B1* | 12/2001 | Dennis et al. | 623/20.14 |
| 6,482,209 B1 | 11/2002 | Engh et al. | |
| 6,749,638 B1 | 6/2004 | Saladino | |
| 6,916,341 B2 | 7/2005 | Rolston | |
| 7,115,131 B2 | 10/2006 | Engh et al. | |
| 7,258,701 B2 | 8/2007 | Aram et al. | |
| 7,520,901 B2 | 4/2009 | Engh | |
| 2001/0039455 A1 | 11/2001 | Simon et al. | |
| 2002/0068979 A1 | 6/2002 | Brown et al. | |
| 2002/0133160 A1 | 9/2002 | Axelson | |
| 2002/0138150 A1 | 9/2002 | Leclercq | |
| 2002/0173852 A1 | 11/2002 | Felt et al. | |
| 2002/0198528 A1 | 12/2002 | Engh et al. | |
| 2003/0069591 A1 | 4/2003 | Carson et al. | |
| 2003/0158606 A1 | 8/2003 | Coon et al. | |
| 2003/0225457 A1 | 12/2003 | Justin et al. | |
| 2004/0102852 A1 | 5/2004 | Johnson et al. | |
| 2004/0153162 A1 | 8/2004 | Sanford et al. | |
| 2004/0167630 A1 | 8/2004 | Rolston | |
| 2004/0204760 A1 | 10/2004 | Fitz et al. | |
| 2005/0043807 A1 | 2/2005 | Wood | |
| 2005/0113846 A1 | 5/2005 | Carson | |
| 2005/0149041 A1 | 7/2005 | McGinley et al. | |
| 2005/0154394 A1 | 7/2005 | Michalowicz | |
| 2005/0165491 A1 | 7/2005 | Diaz | |
| 2005/0171612 A1 | 8/2005 | Rolston | |
| 2006/0004460 A1 | 1/2006 | Engh et al. | |
| 2006/0235290 A1 | 10/2006 | Gabriel et al. | |
| 2007/0078517 A1 | 4/2007 | Engh | |
| 2007/0173858 A1 | 7/2007 | Engh | |
| 2008/0058949 A1 | 3/2008 | Dees et al. | |
| 2009/0222103 A1 | 9/2009 | Fitz et al. | |
| 2010/0145344 A1 | 6/2010 | Jordan et al. | |
| 2011/0184421 A1 | 7/2011 | Dees et al. | |

FOREIGN PATENT DOCUMENTS

| | | |
|---|---|---|
| FR | 2589720 | 5/1987 |
| WO | WO-8702882 | 5/1987 |
| WO | WO2005072629 A1 | 8/2005 |
| WO | WO-2008030842 | 3/2008 |
| WO | WO2008101110 A3 | 10/2008 |

OTHER PUBLICATIONS

Minimally Invasive Surgical Technique, Smith & Nephew ACCURIS Uni Knee System, pp. 1-24 (Mar. 2007).
Surgical Techniques, Smith & Nephew Competitor PFJ Oxinium Patello-Femora Joint with Oxidized Zirconium, pp. 1-25 (Jul. 2006).
Winkelstabilitat, D. Wolter: I. Unidirectional Screw Technology, http://www.litos.com/pages/winkelstabilitaet_e.html, Mar. 3, 2008 (5 pages).
U.S. Appl. No. 90/007,993, Request for Ex Parte Reexamination dated Apr. 4, 2006.
U.S. Appl. No. 90/007,993, Order Denying Ex Parte Reexamination dated May 19, 2006.
U.S. Appl. No. 11/850,178, Restriction Requirement dated Aug. 7, 2009.
U.S. Appl. No. 11/850,178, Non-Final Rejection dated Sep. 29, 2009.
U.S. Appl. No. 11/850,178, Final Rejection dated Apr. 9, 2010.
U.S. Appl. No. 11/850,178, Interview Summary dated Jun. 25, 2010.
International Patent Application No. PCT/US2007/077586, International Search Report and Written Opinion dated May 29, 2008.
International Patent Application No. PCT/US2007/077586, International Preliminary Report on Patentability dated Mar. 19, 2009.
International Search Report for International Application No. PCT/US2008/054003, dated Sep. 1, 2008, 4 pages.
Communication Pursuant to Article 94(3) EPC for European Application No. 08729898.0, dated May 18, 2010, 4 pages.
U.S. Appl. No. 11/850,178, filed Sep. 5, 2007.
U.S. Appl. No. 13/082,112, filed Apr. 7, 2011.
U.S. Appl. No. 12/527,397, filed Feb. 14, 2008.
Office Action for U.S. Appl. No. 11/850,178, dated Oct. 25, 2011.
Patent Examination Report No. 1 for Australian Application No. 2008216173, dated Jul. 4, 2012.
International Preliminary Report on Patentability for International Application No. PCT/US2008/054003, dated Aug. 19, 2009.
Office Action for U.S. Appl. No. 12/527,397, dated Dec. 17, 2012, 6 pages.
Second Office Action for Chinese Application No. 200780041150.5, dated May 30, 2014.
Notice of Reasons for Rejection for Japanese Application No. 2009-527531, dated Jan. 13, 2015.
Patent Examination Report No. 1 for Australian Application No. 2014202464, dated Mar. 17, 2015.
Communication Pursuant to Article 94(3) EPC for European Application No. 07841852.2, dated Jun. 1, 2015.
Examination Report No. 1 for Standard Patent Application issued in Australian Application No. 2016201717 dated May 18, 2017.
Communication Pursuant to Article 94(3) EPC for European Application No. 07841852.2 dated Mar. 5, 2014.
Third Office Action for Chinese Application No. 200780041150.5, dated Mar. 4, 2015.

* cited by examiner

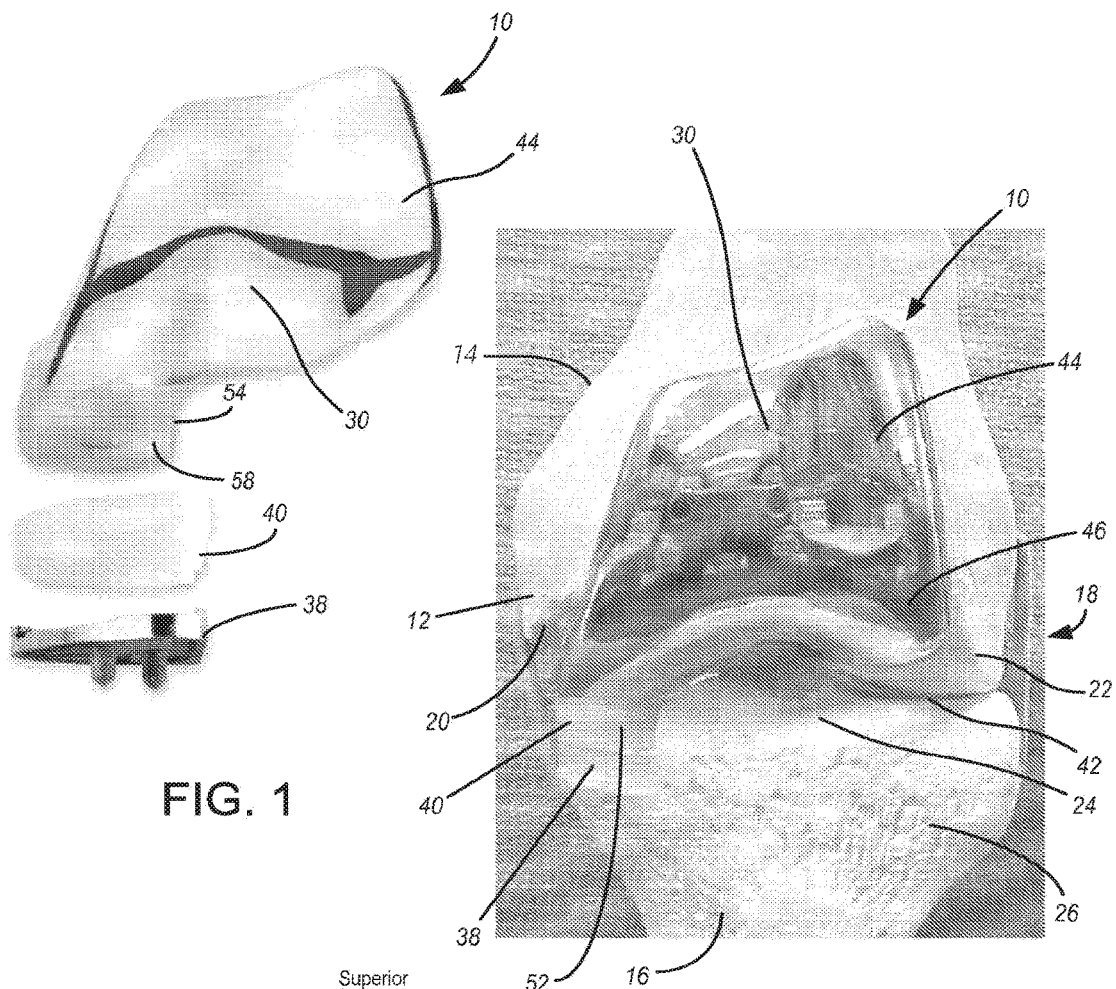
FIG. 1
FIG. 2A
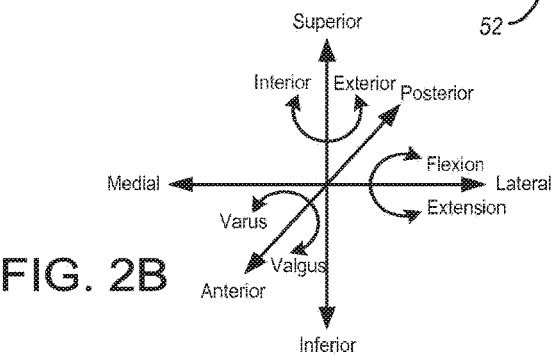
FIG. 2B

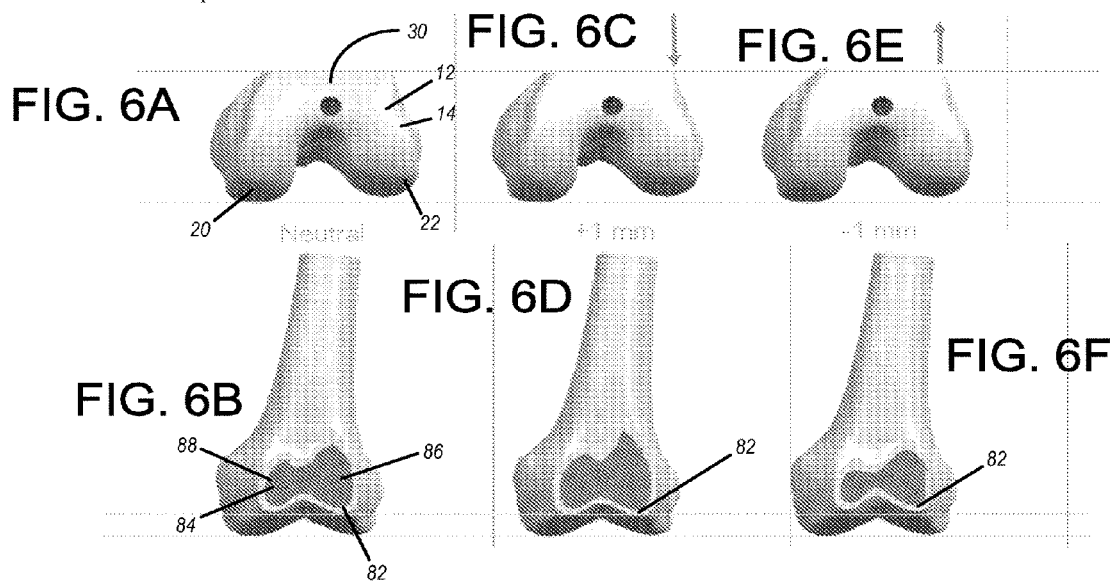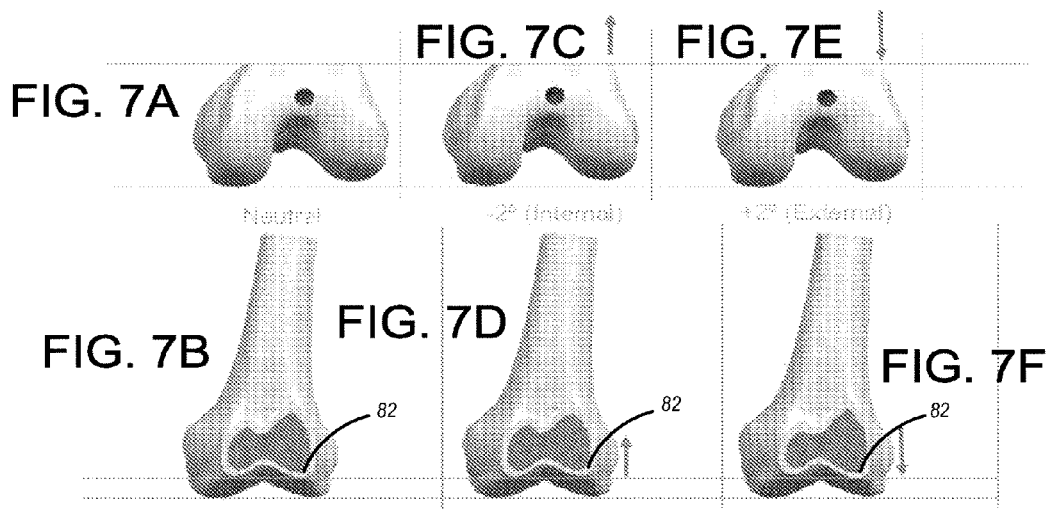

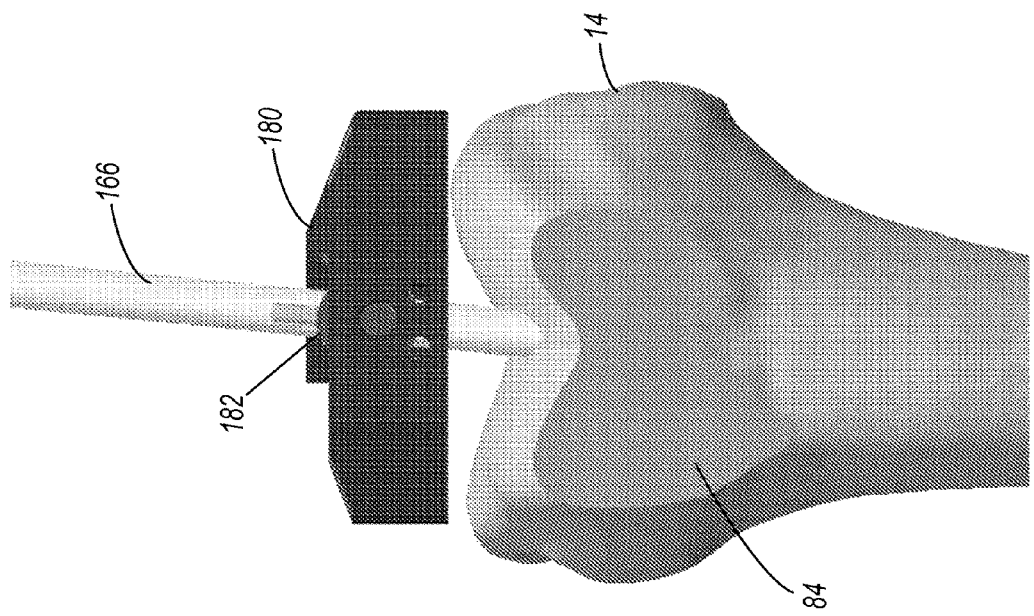
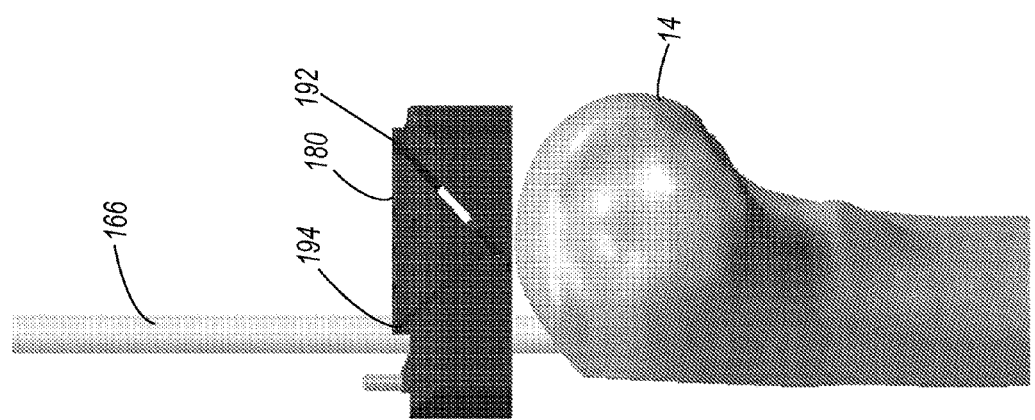
FIG. 42B
FIG. 42A

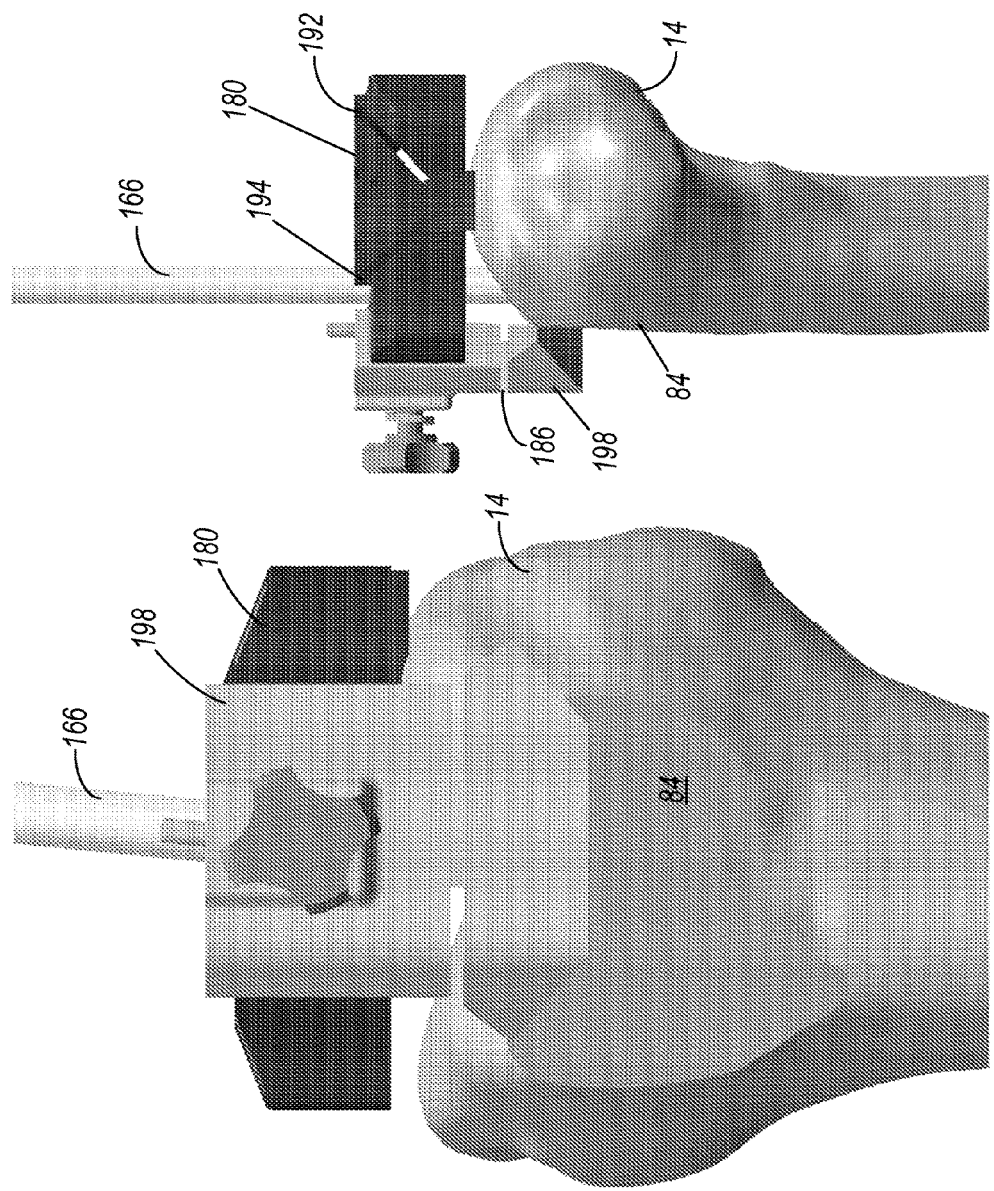

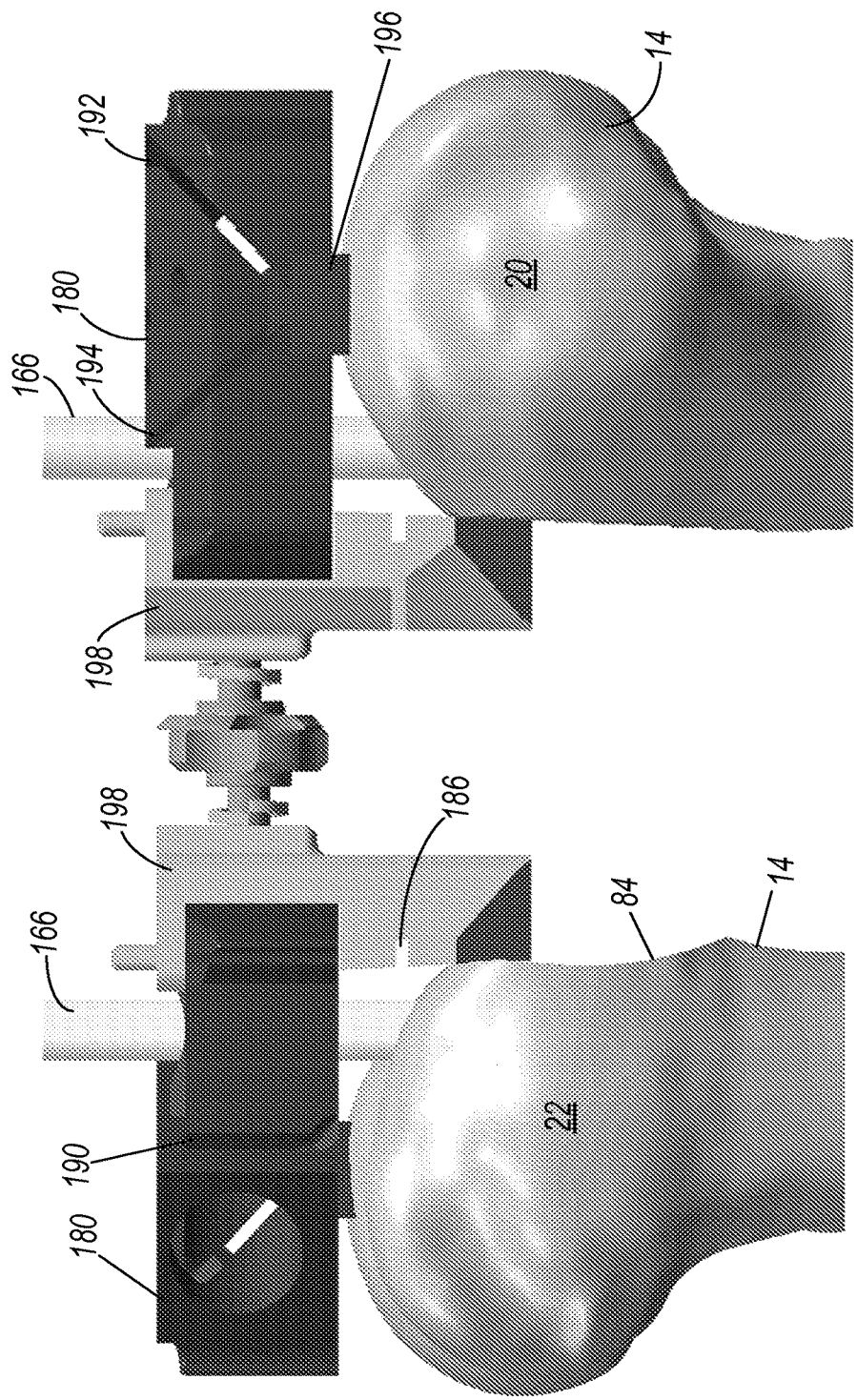

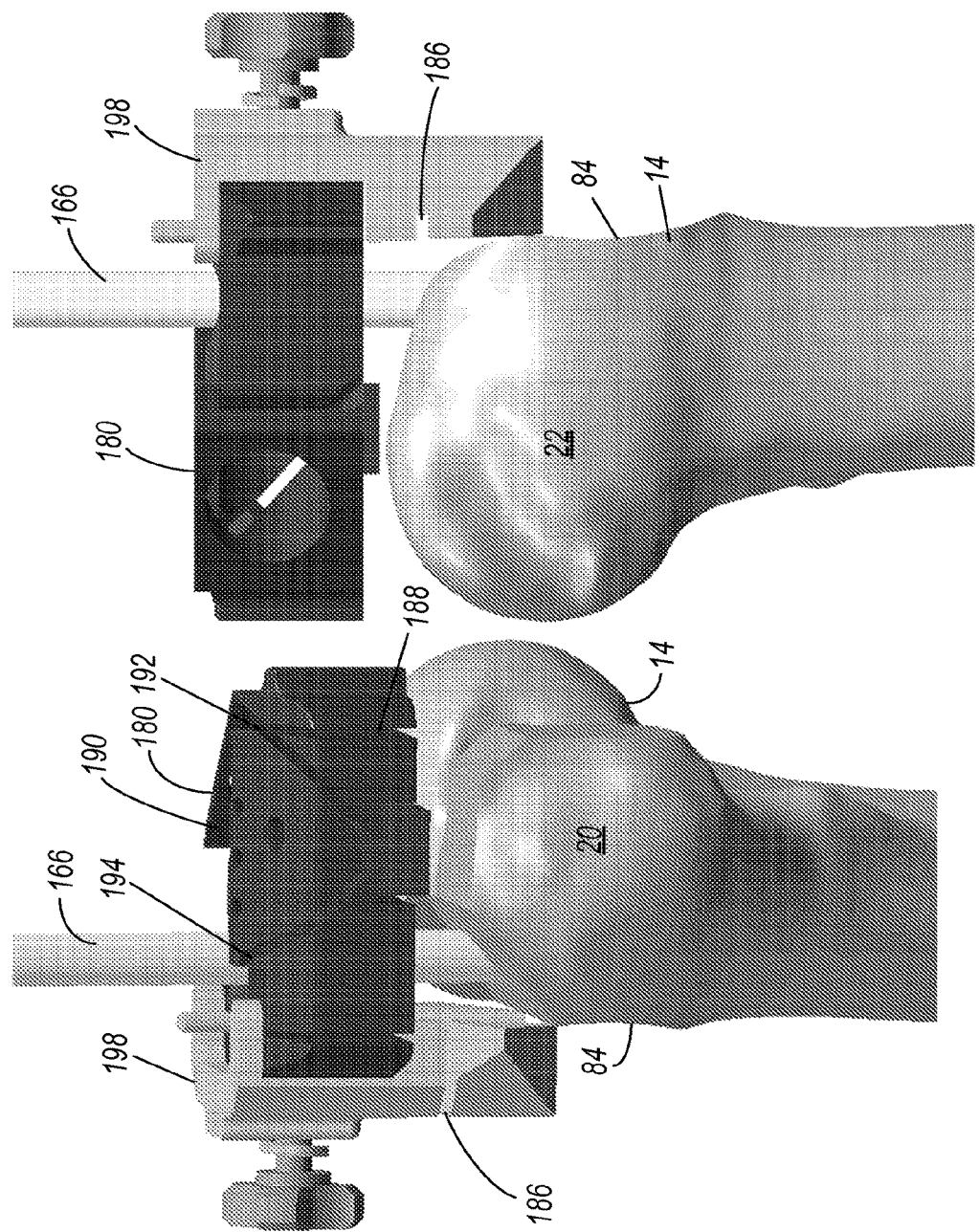

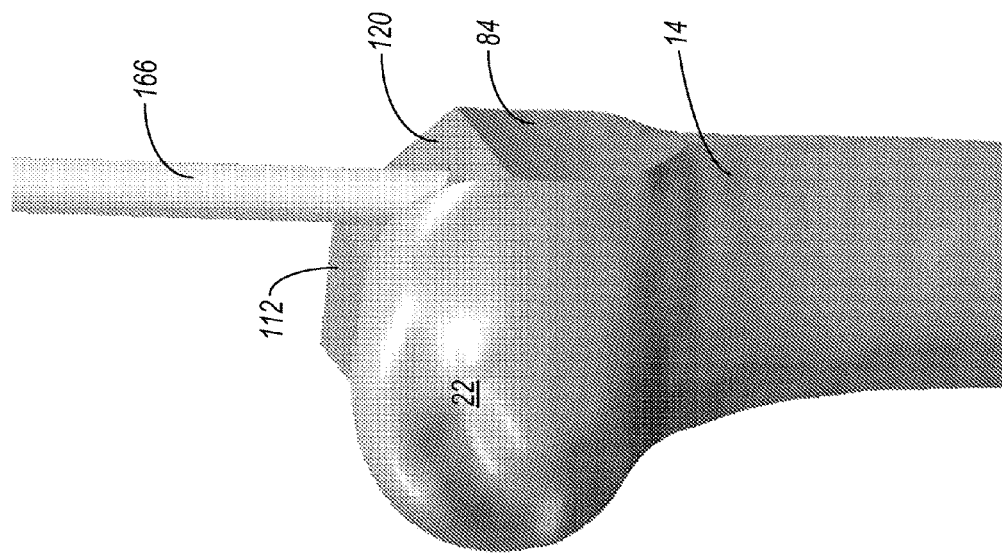
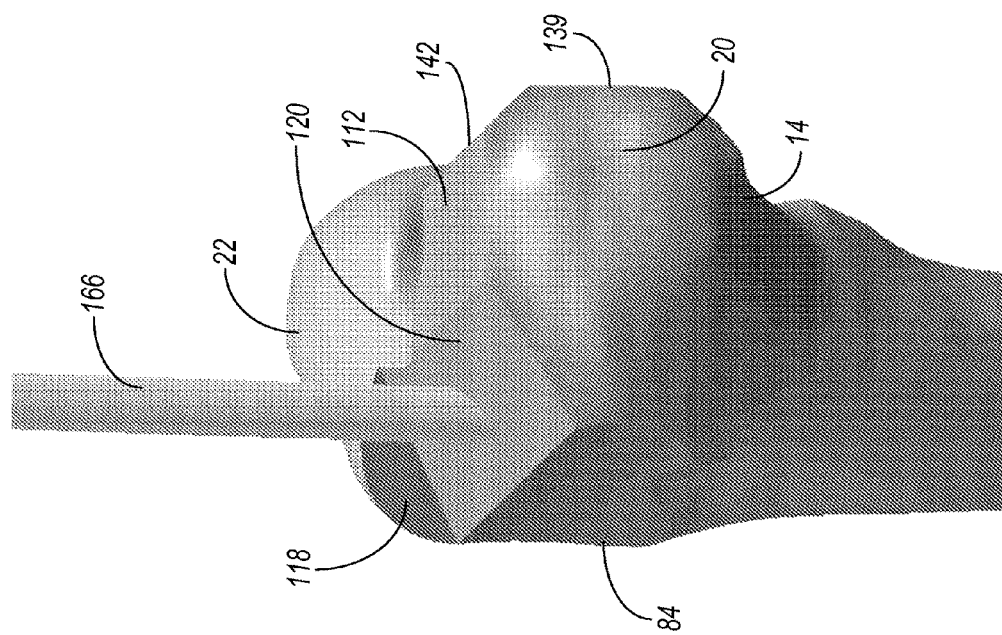
FIG. 49A
FIG. 49B

IMPLANTS WITH TRANSITION SURFACES AND RELATED PROCESSES

This application is a divisional of U.S. application Ser. No. 11/850,178, filed Sep. 5, 2007, titled "Implants With Transition Surfaces and Related Processes," which claims the benefit of U.S. Provisional Application Ser. No. 60/828,158, filed Oct. 4, 2006, titled "Instrumentation for Bicompartmental Knee," U.S. Provisional Application Ser. No. 60/825,533 filed Sep. 13, 2006, titled "Variable Transition Referencing Guide," and U.S. Provisional Application Ser. No. 60/824,696, filed Sep. 6, 2006, titled "Instrumentation for Bicompartmental Knee," the entire contents of each of which are hereby incorporated by reference.

FIELD OF THE INVENTION

The invention relates to implants and processes for use in joint surgery, particularly knee replacement surgery. In certain embodiments, methods are provided for locating and using a transition point on the femur for proper positioning of resections that are intended to receive a femoral component during a surgical procedure. Implants are provided according to certain embodiments that replace the medial condyle and part of the patellofemoral channel of the femur, but preferably do not replace portions of the lateral condyle that articulate with respect to the tibia. According to certain embodiments, a resection guide that includes a guide surface for performing a transition resection can be positioned relative to the resections on the bone formed using the transition point. The resection guide can then be moved on the resection surfaces to position the transition resection guide surface to form a transition resection that allows implant external surfaces to transition smoothly to portions of the lateral condyle that articulate with respect to the tibia.

BACKGROUND

Knee arthritis and trauma in various forms can cause loss of joint cartilage, including for example, osteoarthritis, excessive wear or sudden trauma, rheumatoid arthritis, or infectious arthritis. When joint cartilage is worn away, the bone beneath the cartilage is left exposed, and bone-on-bone contact can be very painful and damaging. Other types of problems can occur when the bone itself becomes diseased. One conventional solution for these types of joint problems takes the form of total knee replacements. In a total knee replacement (TKR), the proximal end of the tibia is replaced with a tibial component, the distal end of the femoral bone is replaced with a femoral component, and the patella is replaced with a patellar component. Such procedures often require sacrifice of the anterior and posterior cruciate ligaments.

However, many patients who develop knee arthritis experience issues isolated to the medial (inner) compartment and the patellofemoral (knee cap) part of the joint, while the lateral (outer) compartment of the joint remains healthy. The conventional treatment for such patients is either the combination of a unicompartmental knee in conjunction with a patellofemoral implant or the use of a total knee implant, which requires removal of the healthy lateral condyle. However, one recent solution is a hybrid femoral component that preserves the healthy lateral condyle as well as the anterior and posterior cruciate ligaments, and only replaces the medial compartment and patellofemoral joint. (Such a hybrid femoral component may be used in conjunction with a unicompartmental tibial tray, which only requires resurfacing of part of the tibia as well). A hybrid femoral component requires a smaller incision and preserves ligaments that can help the knee retain its natural kinematics. It can be implanted using a procedure called a bicompartmental knee replacement.

A bicompartmental knee replacement is a procedure that replaces only the medial (inner) parts of the femoral and tibial components. It does not resurface or resect the lateral parts of the knee (including the distal femoral articular cartilage), and as such, can allow the anterior and posterior cruciate ligaments to be retained. Bicompartmental knee replacements have a number of advantages over total knee replacements. Because the outer lateral portion of the joint is not resurfaced, the incision made may be smaller, resulting in less pain, quicker recovery time, and less blood loss. Also, because certain ligaments do not need to be sacrificed, a greater stability of the knee can be maintained.

The femoral component used in such a replacement is often called a monolithic implant. It has an anterior portion and a medial condyle portion, without a lateral condyle portion (again, because as much of the lateral bone as possible is retained). As with most typical femoral implants, the component may be made of titanium, stainless steel, cobalt-chrome, zirconium, oxinium, any combination thereof, or any other appropriate material that has sufficient strength and biocompatibility for use in knee replacement surgery.

While performing bicompartmental knee replacement with a monolithic implant, it is necessary to locate the implant on the bone properly, in order, among other things, to achieve proper articulation in both the medial and lateral compartments of the knee between femur and tibia, as well as proper articulation between the patella and the femur or femoral component interface. For example, the surgeon wants to retain as much healthy bone as possible while removing the diseased bone, but also needs to consider the depth of the medial condyle portion of the implant in order to ensure that there is a smooth transition from the implant to the bone and to maintain proper performance of the reconstructed knee in flexion and extension.

With conventional patellofemoral replacements, one popular current method for preparing the bone to receive an implant is to use an osteotome in conjunction with a trochlea trial to mark the boundary of the transition between the implant and the bone. However, there is no known solution or method for marking the boundary for bicompartmental knee replacement. Accordingly, such surgeries are conventionally performed using traditional total knee replacement instrumentation, without any additional components that help identify certain reference points. For example, recessing the implant to the cartilage on the lateral side is important, and without specific instrumentation or techniques for this type of procedure, the surgeon is left to estimate the cuts that are needed.

SUMMARY

Implants and processes for installing them are provided for replacing the medial condyle of the femur and portions of the patellofemoral channel, preferably without replacing portions of the lateral condyle which have not been subject to degradation. According to some such processes, instrumentation may be used which allows for an anterior resection and a distal resection of the femur that are properly located and oriented so that proper positioning of the implant to ensure smooth transition between bone and implant on lateral outer surfaces of the femur, as well as proper functioning of the reconstructed knee in flexion and extension, can be reduced to determining the proper medial/lateral position of the implant on those resections.

In some cases, an anterior resection instrument can be used to form an anterior resection that is properly located in the anterior/posterior dimension and in interior/exterior rotation relative to the femur. A transition point can then be chosen, which can correspond if desired to the distal-most point on a lateral portion of the anterior resection, for proper proximal/distal or superior/inferior location and valgus/varus rotation of a distal resection. A distal resection guide, of a type which can be used with cutting devices such as saws, or of a type which can be used with milling devices, or a type which can be used with both, and which can be positioned and oriented relative to the transition point may be used to perform this distal resection of the medial condyle. Alternatively, a single such instrument can be used to perform the anterior resection and the distal resection.

In some cases, an additional resection guide can be used which can be positioned properly on the anterior resection and the distal resection and then slid or otherwise manipulated medially or laterally to determine proper location of a transition resection which will help form the transition between implant and bone on outer surfaces of lateral portions of the femur. Alternatively, one or more of the transition resection guide surface, the distal resection guide surface, and also the anterior resection guide surface can be included in one instrument or resection guide.

In some cases, implants adapted to be installed on such resected femurs feature a transition surface which corresponds to the transition resection that has been controllably located and oriented relative to the femur as mentioned above. Such a transition when properly located aims to create a smooth transition from implant surface to bone surface by, among other things, reducing surface discontinuity such as implant and/or bone overhang. Preferably, the transition between bone and implant in such cases is located so that only anatomical lateral condyle surfaces articulate relative to the tibia in the knee joint in which the implant has been installed.

BRIEF DESCRIPTION

FIG. 1 is a front view of an implant according to certain embodiments of the invention.

FIG. 2A is a front view of the implant of FIG. 1 in place on a model of a human knee.

FIG. 2B is a navigational rose showing translational and rotational axes which may constitute useful references in positioning and orienting body parts, instruments and implants of certain embodiments of the invention.

FIGS. 6A-6F are schematic distal and front views of human femurs on which anterior resections according to one embodiment of the invention have been performed, and which show effect of depth of the anterior resection on its shape and size.

FIGS. 7A-7F are schematic distal and front views of human femurs on which anterior resections according to one embodiment of the invention have been performed, and which show effect of internal/external rotation of the anterior resection on its shape.

Figure 10:
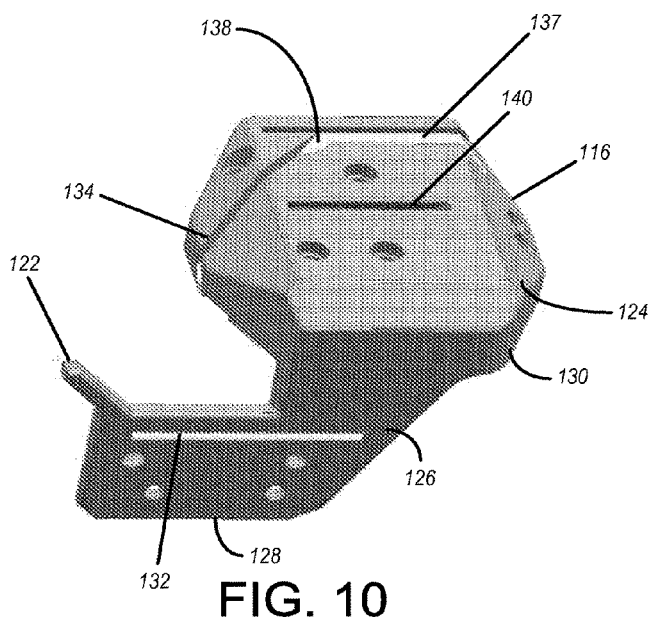
FIG. 10 is a perspective front view of an anterior/posterior resection guide according to one embodiment of the invention.
Figure 11:
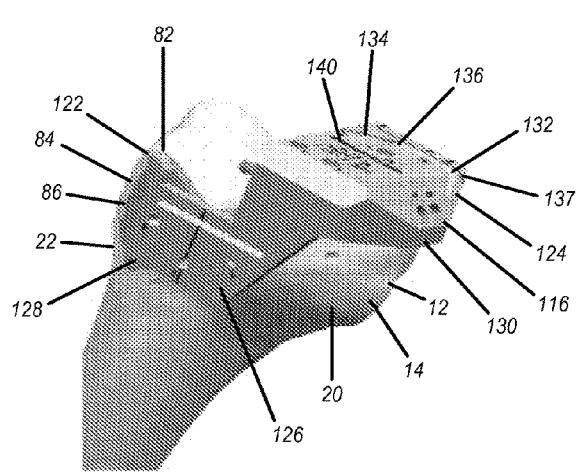

FIG. 11 is a perspective medial view showing the resection guide of FIG. 10 in place on a human femur, in contact with the anterior resection and the medial condyle distal resections, so that it can be positioned (as by sliding) medially or laterally on the femur in contact with those resections, to position the transition cutting surface of the resection guide in order to yield a smooth transition between implant and bone on the lateral side of the knee.

Figure 12:
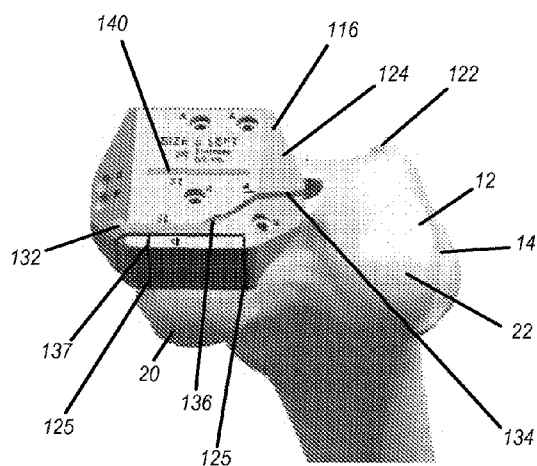

FIG. 12 is a perspective posterior view of the resection guide of FIGS. 10 and 11 in place on a human femur.

Figure 13:
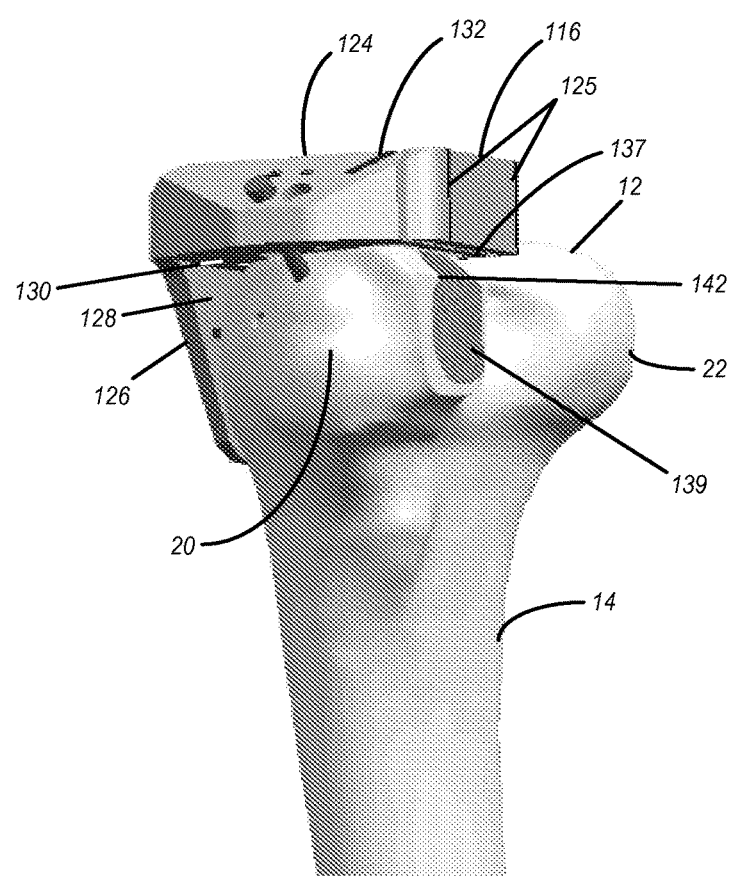

FIG. 13 is a perspective medial side view of the resection guide of FIGS. 10-12 in place on a human femur.

Figure 14:
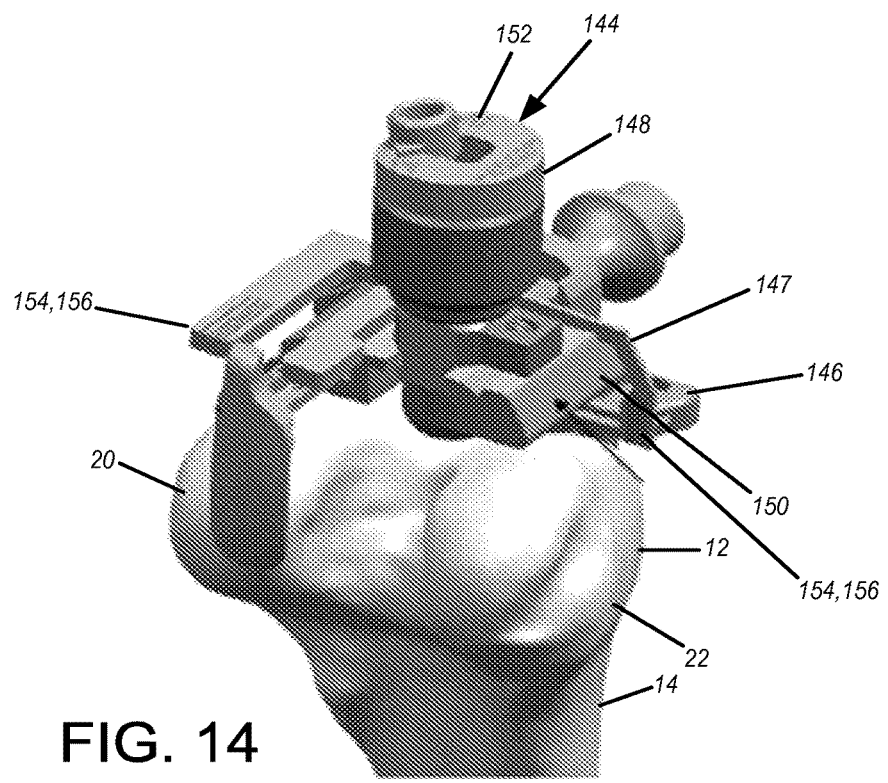

FIG. 14 is a perspective medial front view of a resection guide according to another embodiment of the invention positioned on a human femur.

Figure 15:
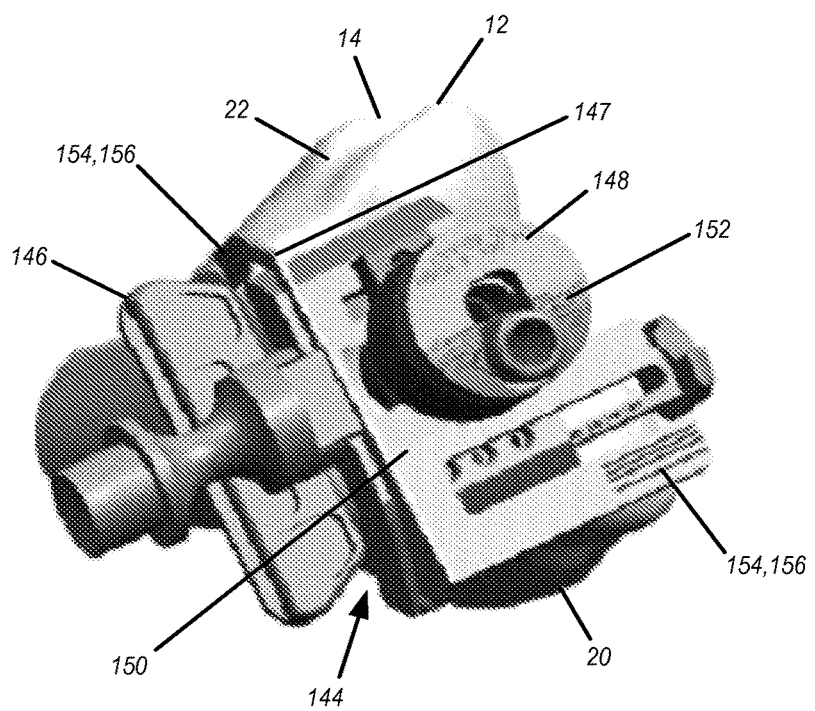

FIG. 15 is a perspective top view of the resection guide of FIG. 14 positioned on a human femur.

Figure 16:
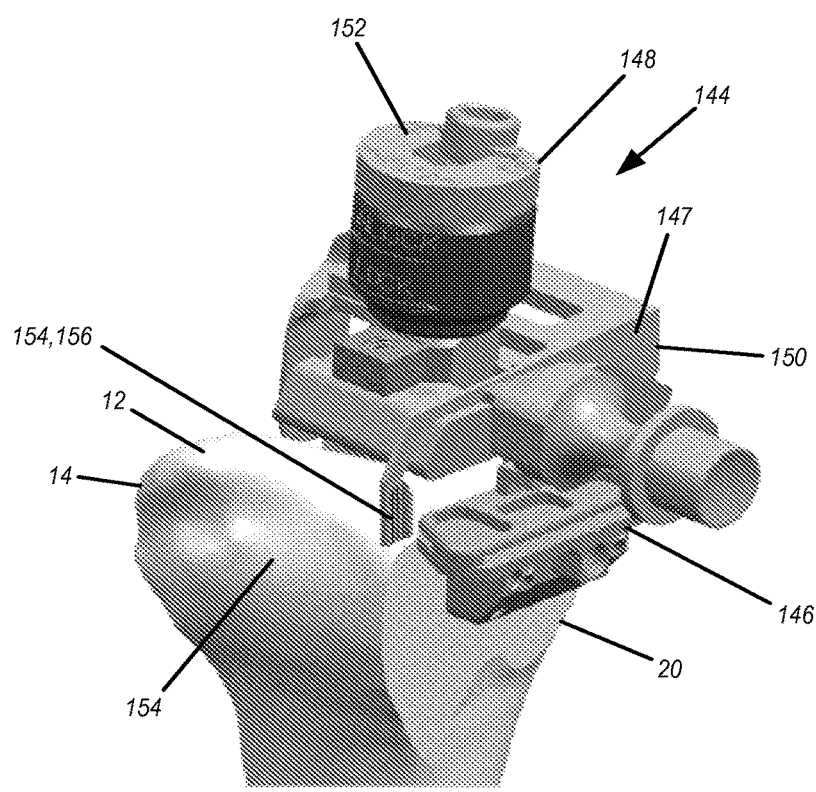

FIG. 16 is a perspective lateral front view of the resection guide of FIG. 14 positioned on a human femur.

Figure 17:
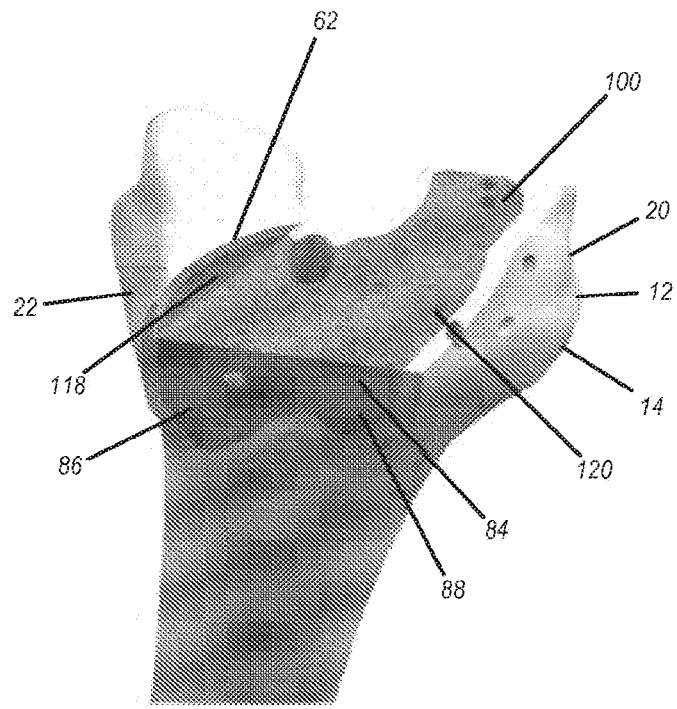

FIG. 17 is a perspective medial front view showing a human femur on which anterior, distal, chamfer and transition resections have been made according to one embodiment of the invention, using resection guides according to certain embodiments of the invention.

Figure 18:
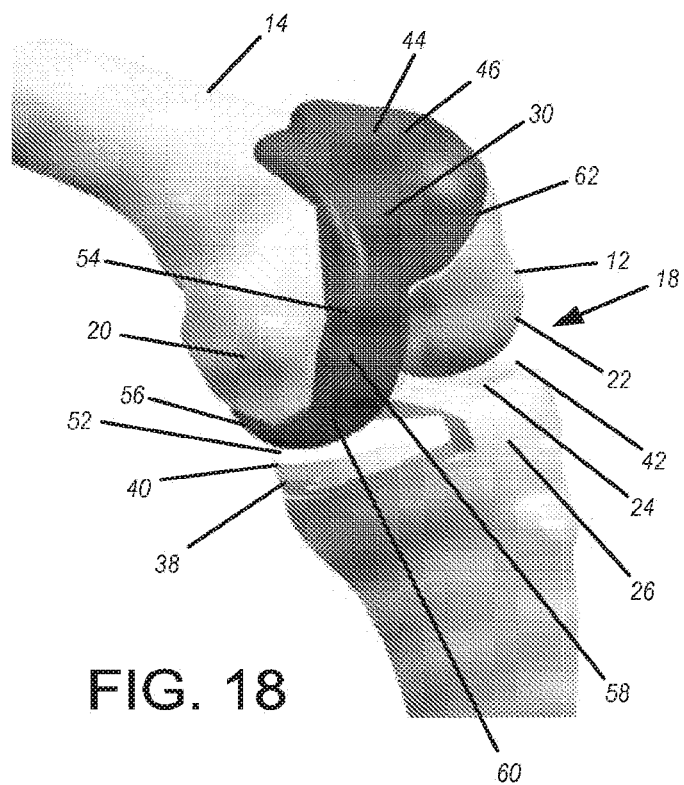

FIG. 18 is a perspective medial front view showing an implant according to one embodiment of the invention in place on a femur.

Figure 19:
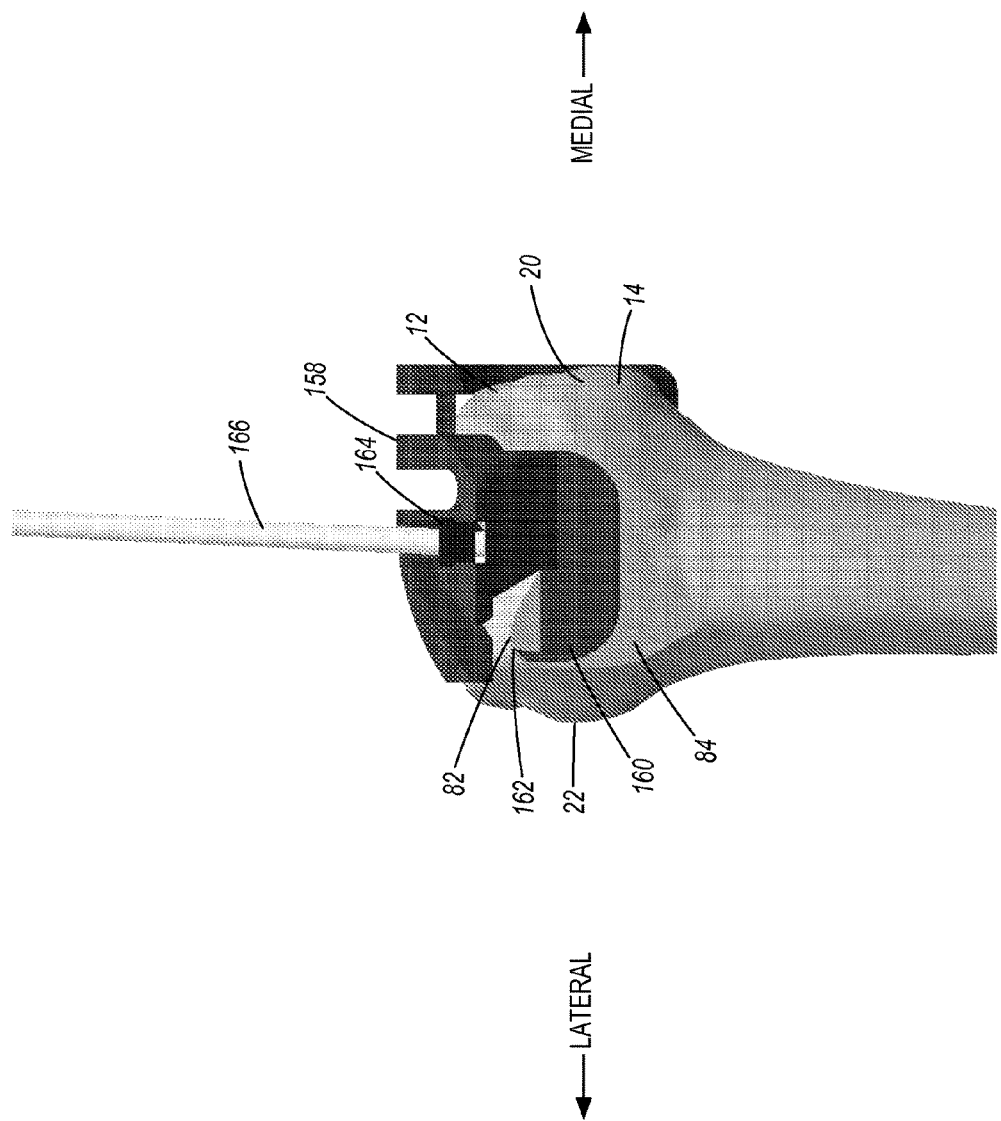

FIG. 19 is a front view of a resection guide according to an alternate embodiment of the invention, for use with milling devices for forming resections on the femur.

Figure 20:
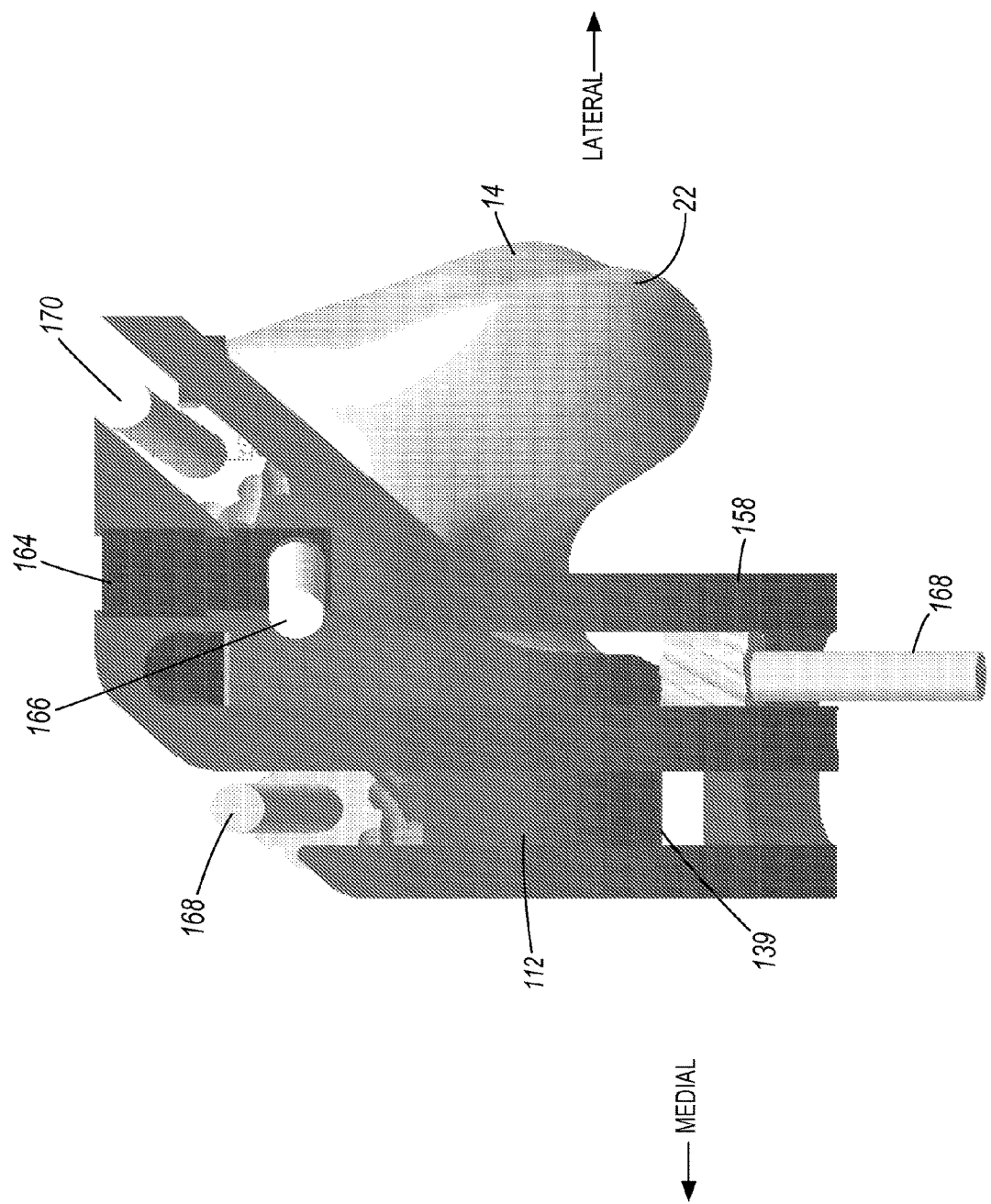

FIG. 20 is a superior view of the guide of FIG. 19 showing certain milling devices.

Figure 21:
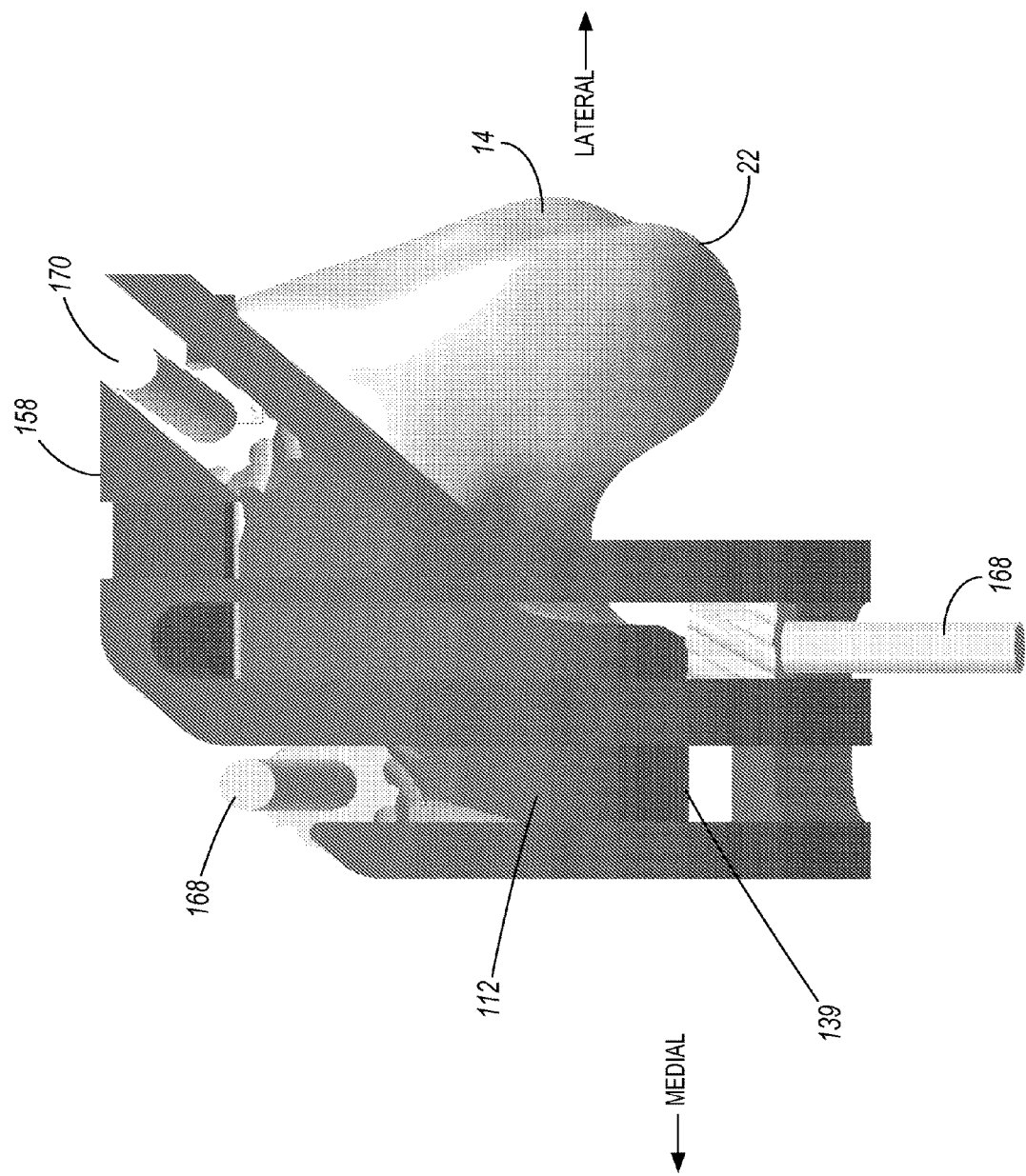

FIG. 21 is a superior view of the guide of FIG. 19 without an intramedullary rod.

Figure 22:
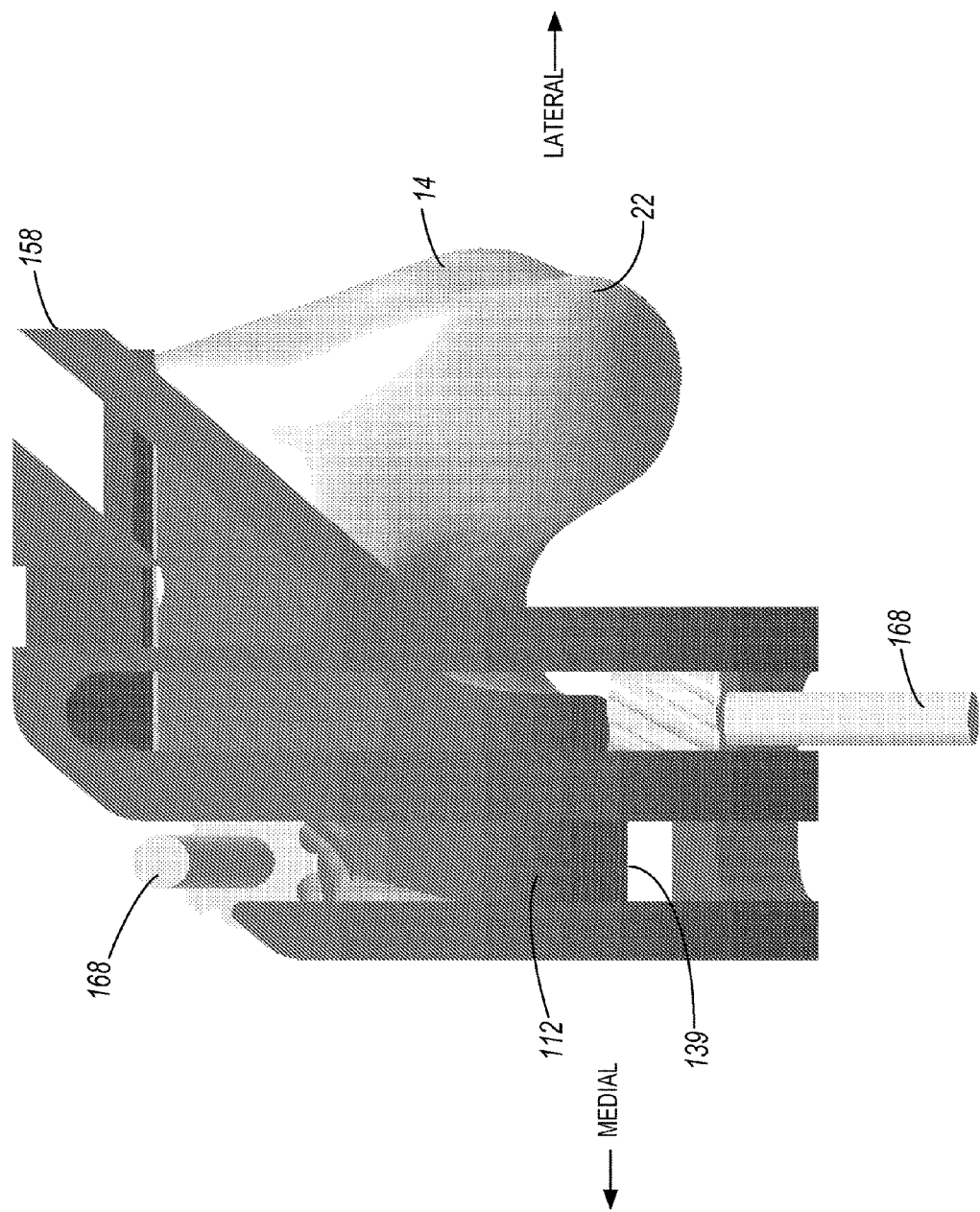

FIG. 22 is another superior view of the guide of FIG. 19.

Figure 23:
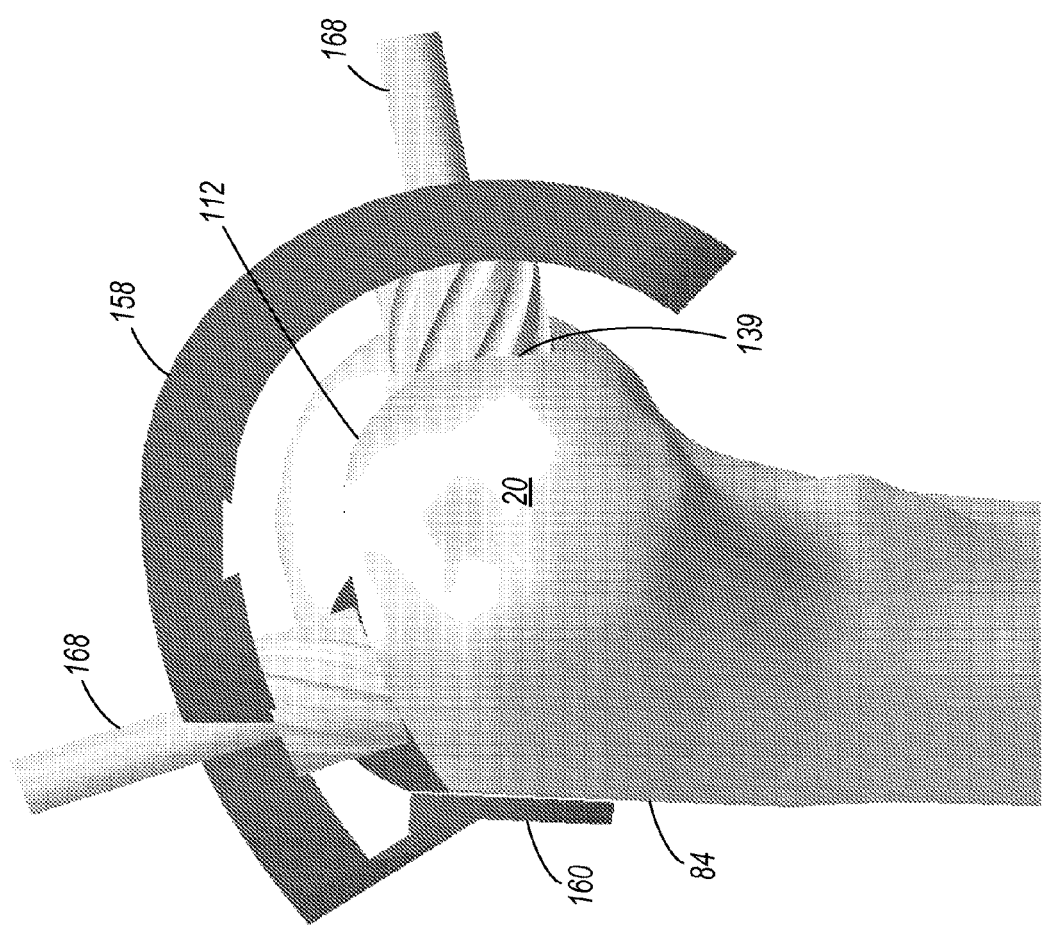

FIG. 23 is a side view of the guide of FIG. 19.

Figure 24:
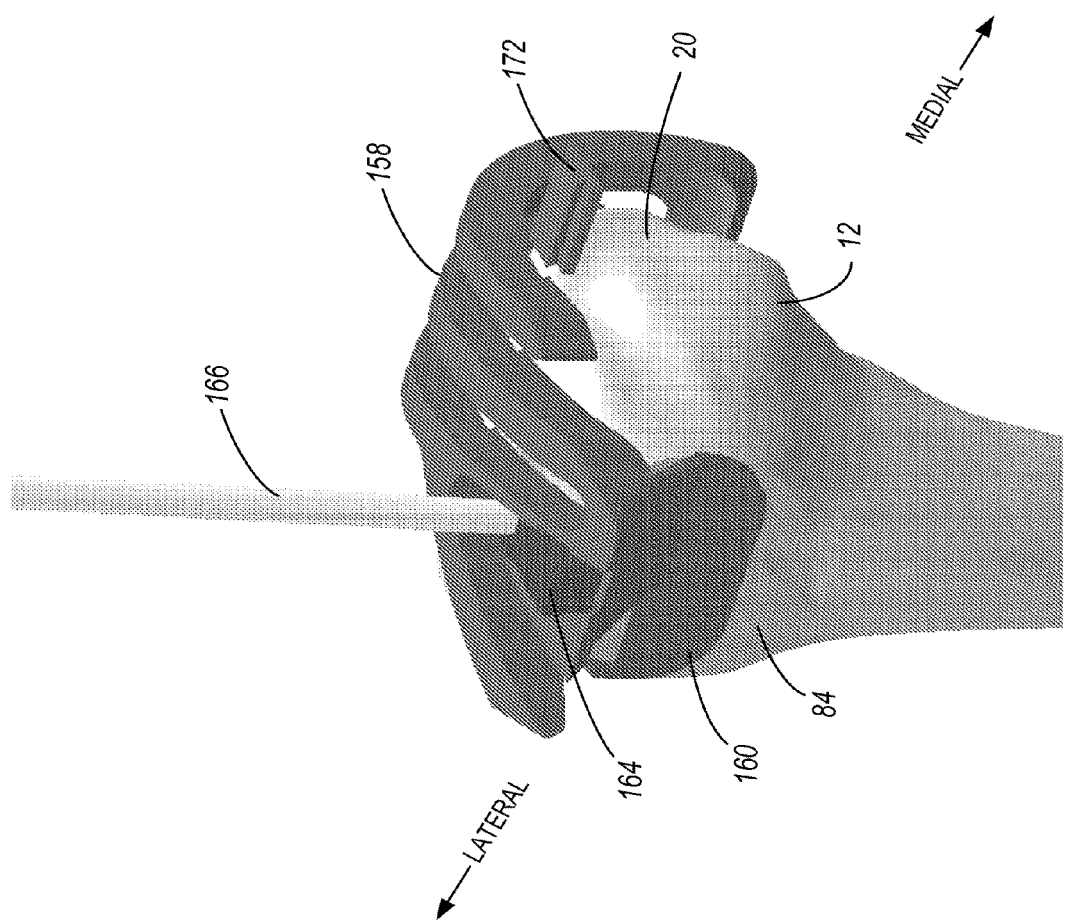

FIG. 24 is a perspective view of the guide of FIG. 19.

Figure 25:
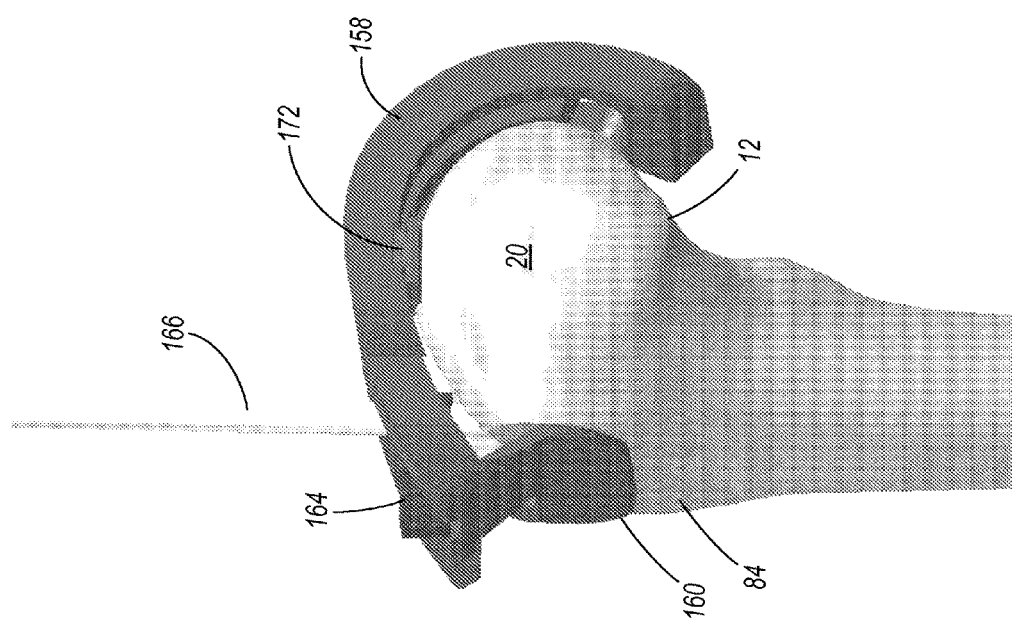

FIG. 25 is a side perspective view of the guide of FIG. 19.

Figure 26:
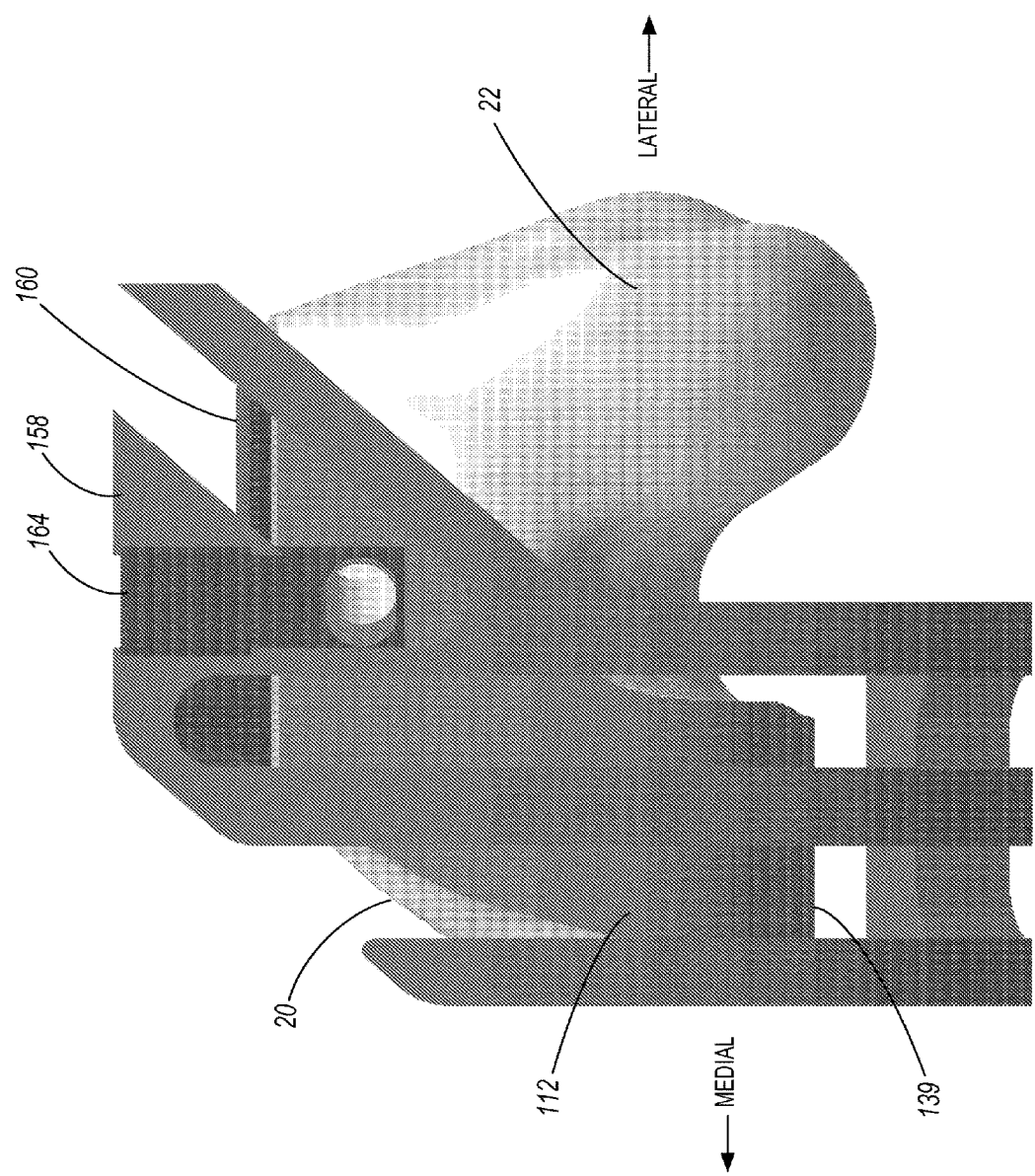

FIG. 26 is a superior view of a guide according to another alternate embodiment of the invention.

Figure 27:
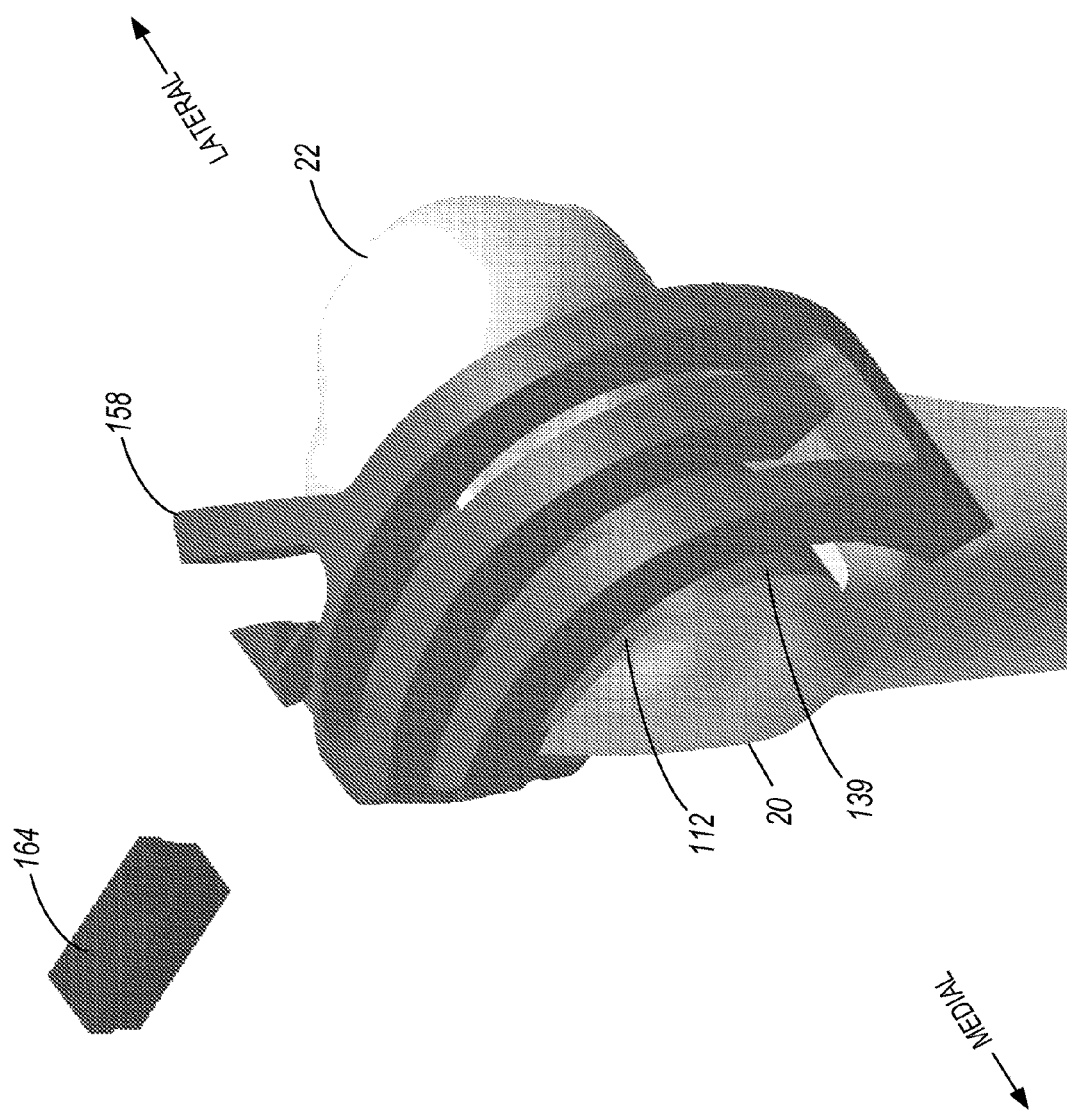

FIG. 27 is a perspective view of the guide of FIG. 26.

Figure 28:
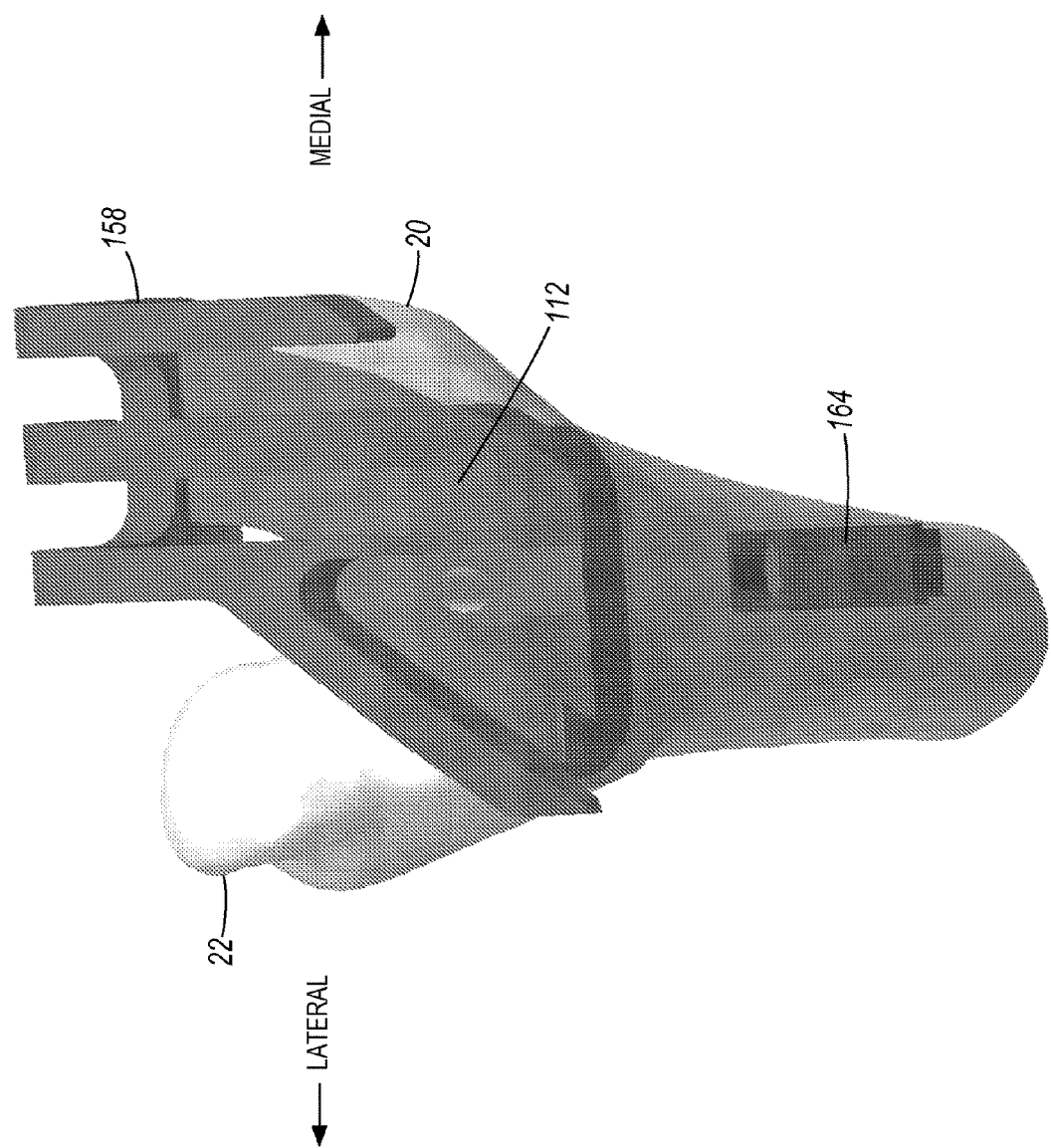

FIG. 28 is a superior view of the guide of FIG. 26.

Figure 29:
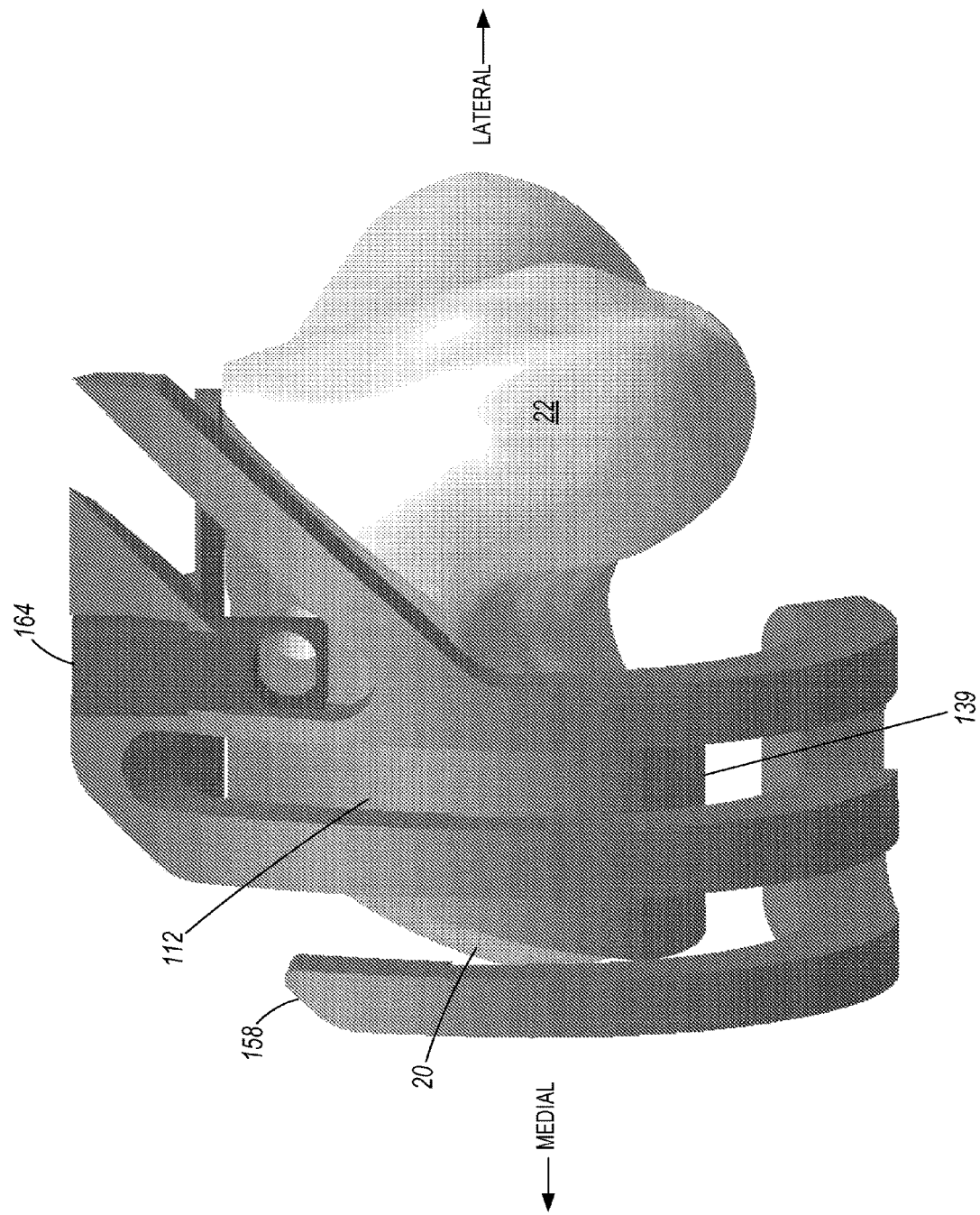

FIG. 29 is a superior view of the guide of FIG. 26.

Figure 30:
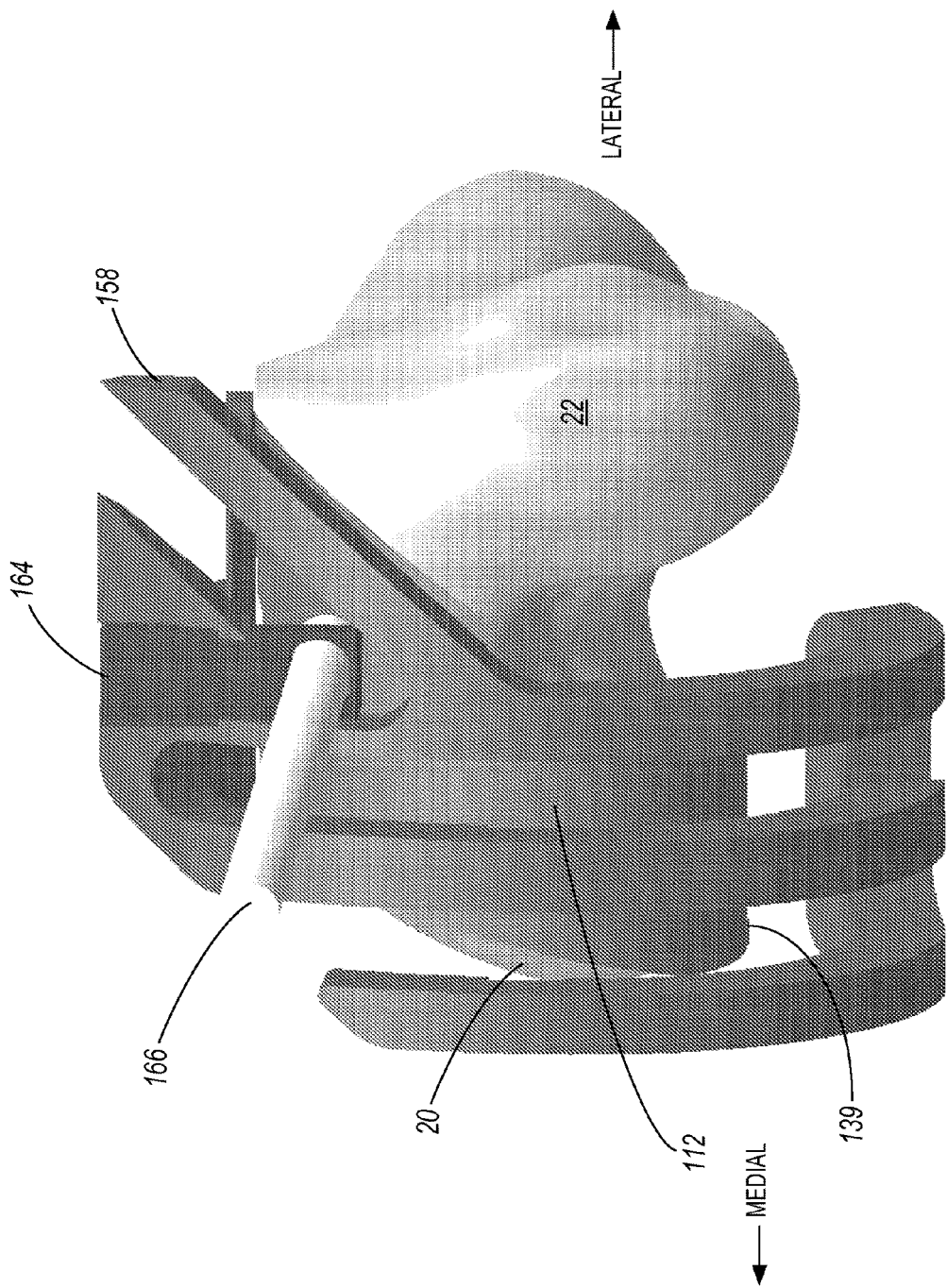

FIG. 30 is a superior view of the guide of FIG. 26.

Figure 31:
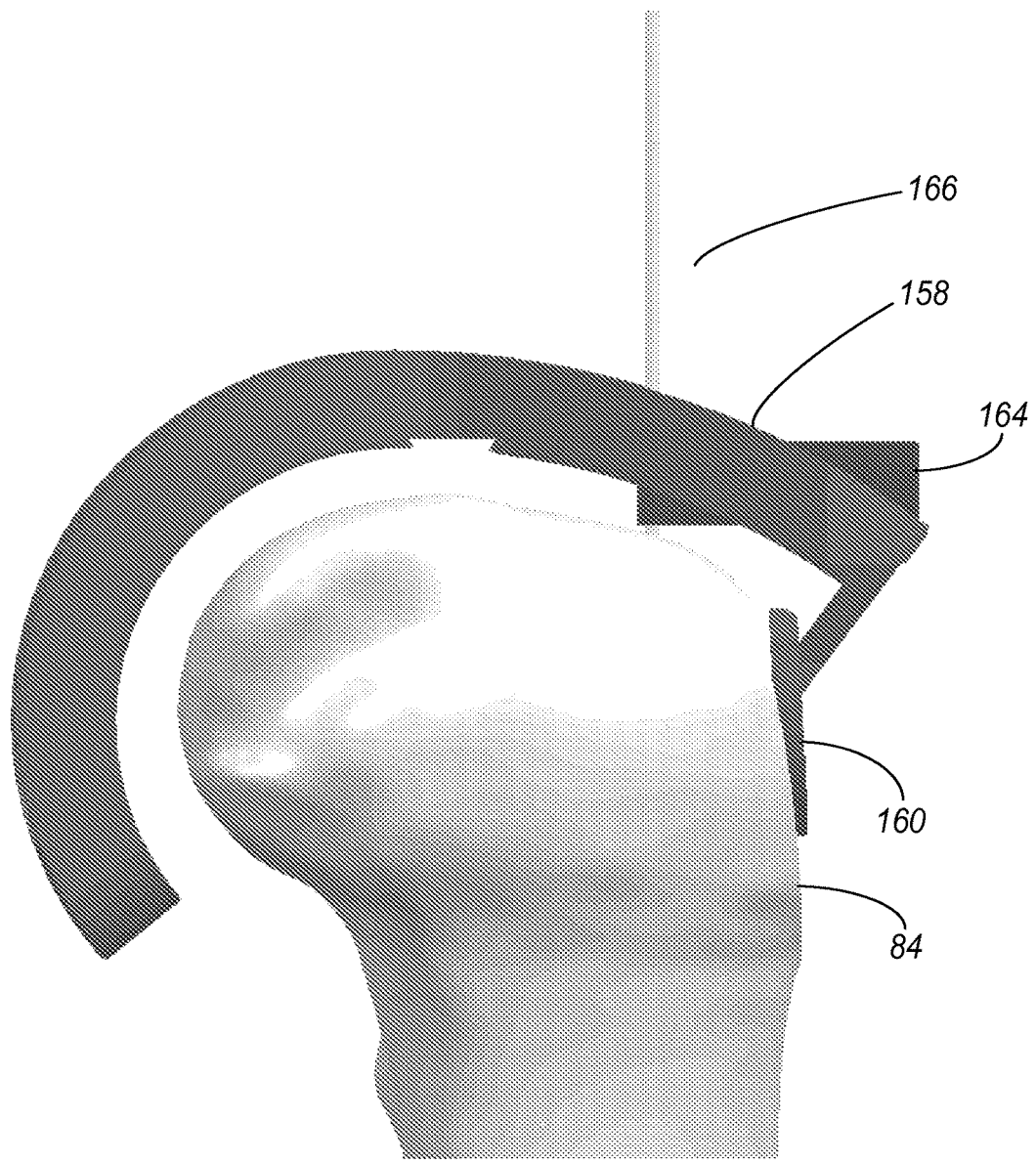

FIG. 31 is a side view of the guide of FIG. 26.

Figure 32:
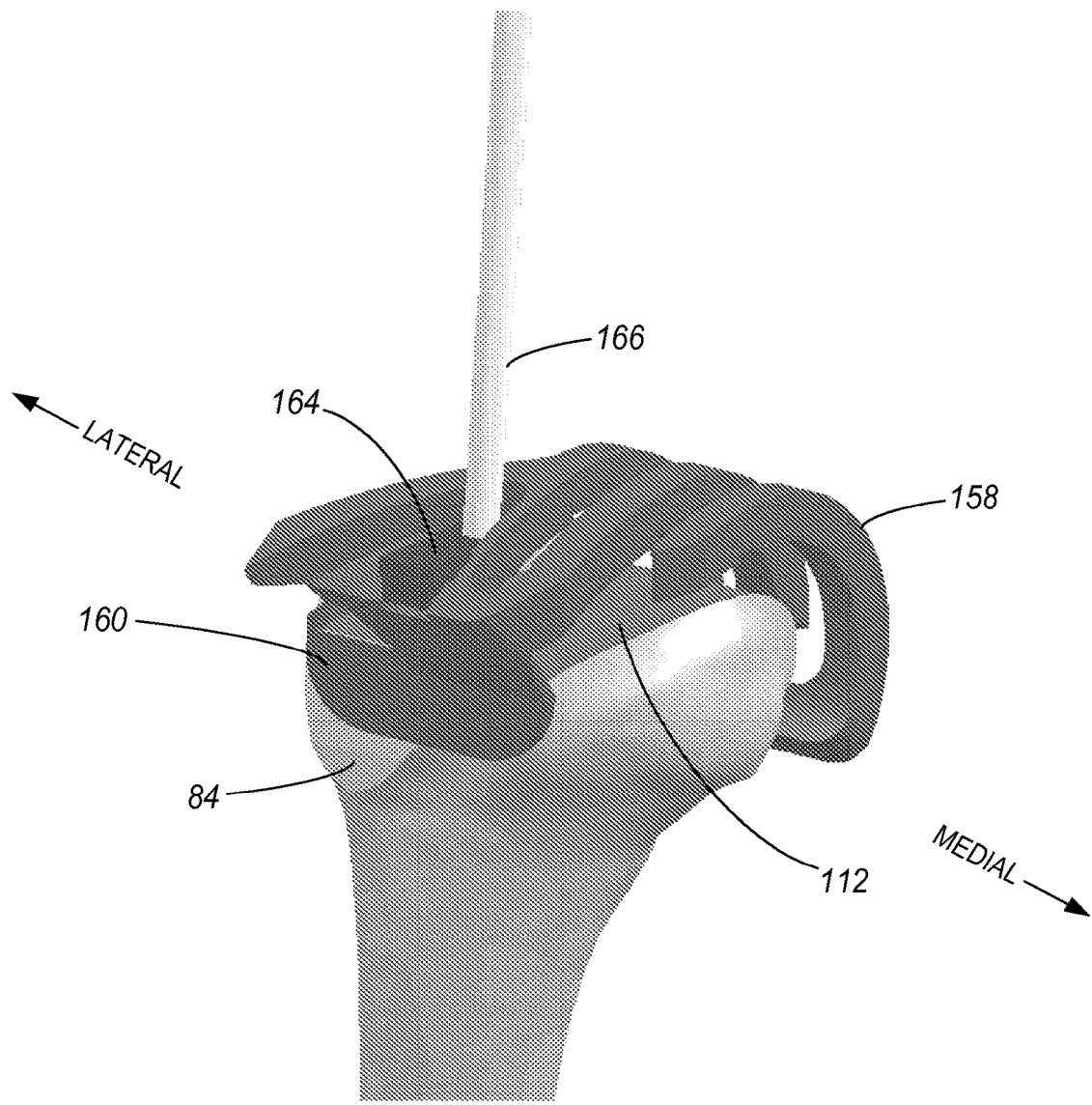

FIG. 32 is a perspective view of the guide of FIG. 26.

Figure 33:
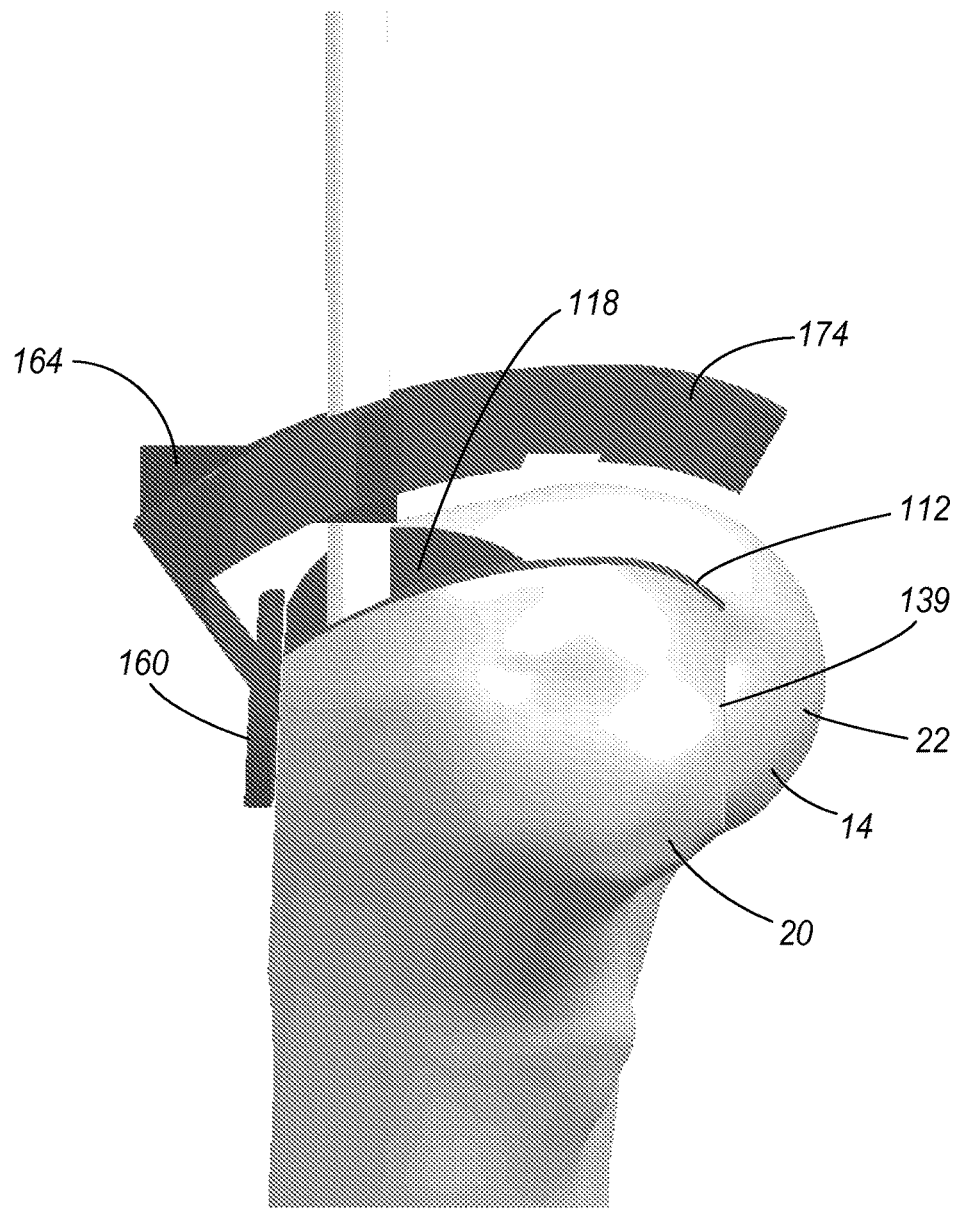

FIG. 33 is a side view of a guide according to another alternate embodiment of the invention.

Figure 34:
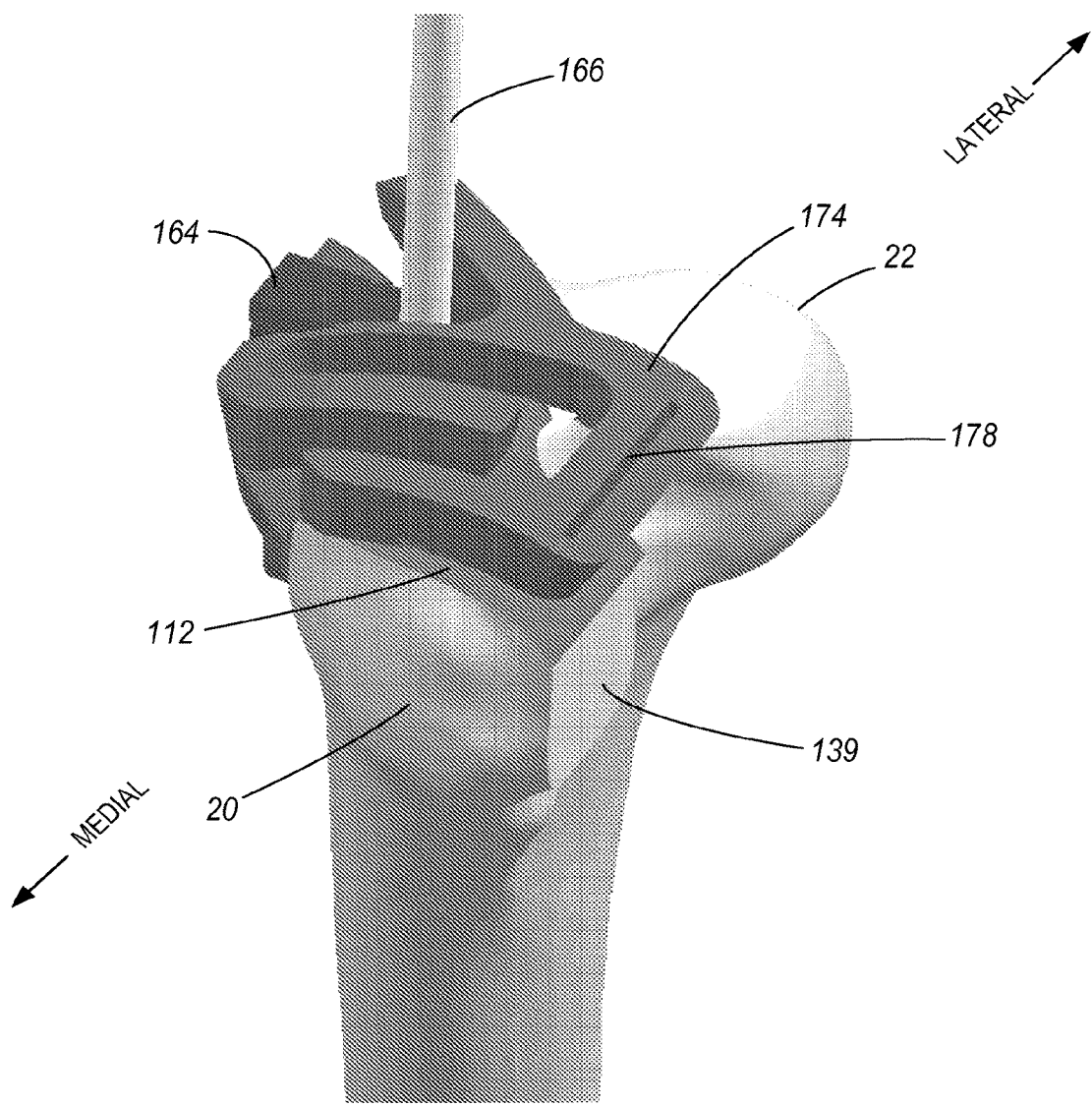

FIG. 34 is a perspective view of the guide of FIG. 33.

Figure 35:
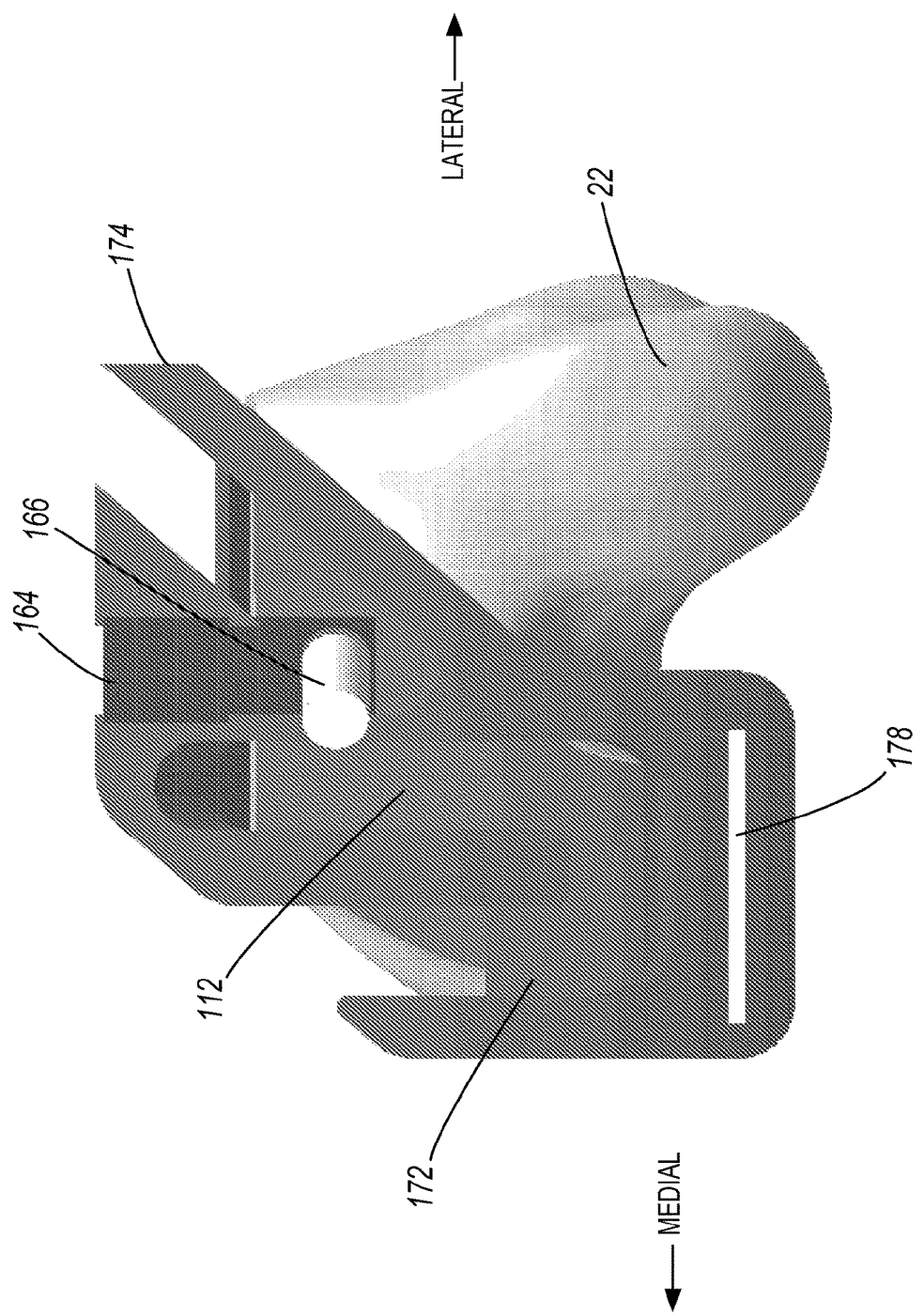

FIG. 35 is a superior view of the guide of FIG. 33.

Figure 36:
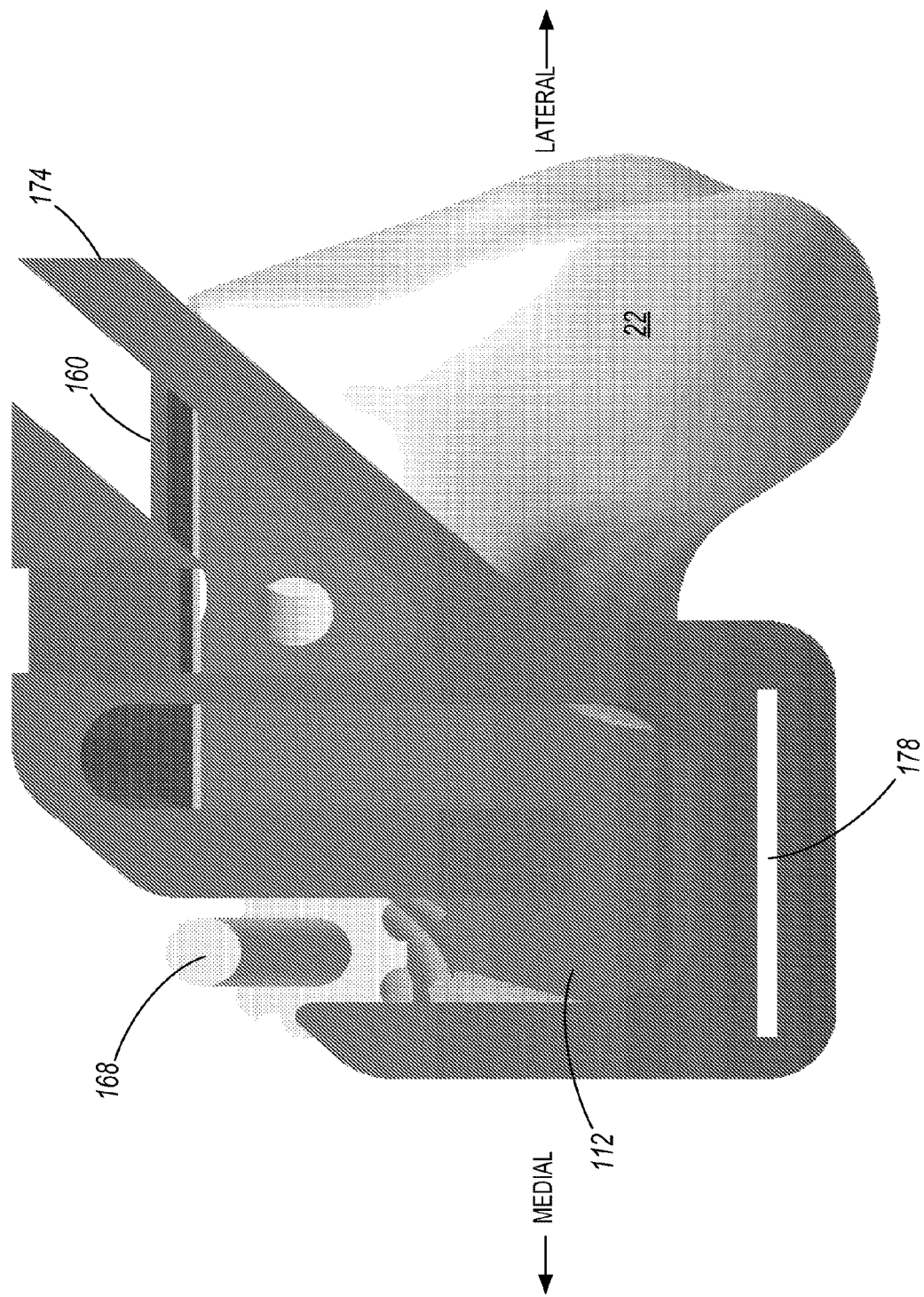

FIG. 36 is a superior view of the guide of FIG. 33.

Figure 37:
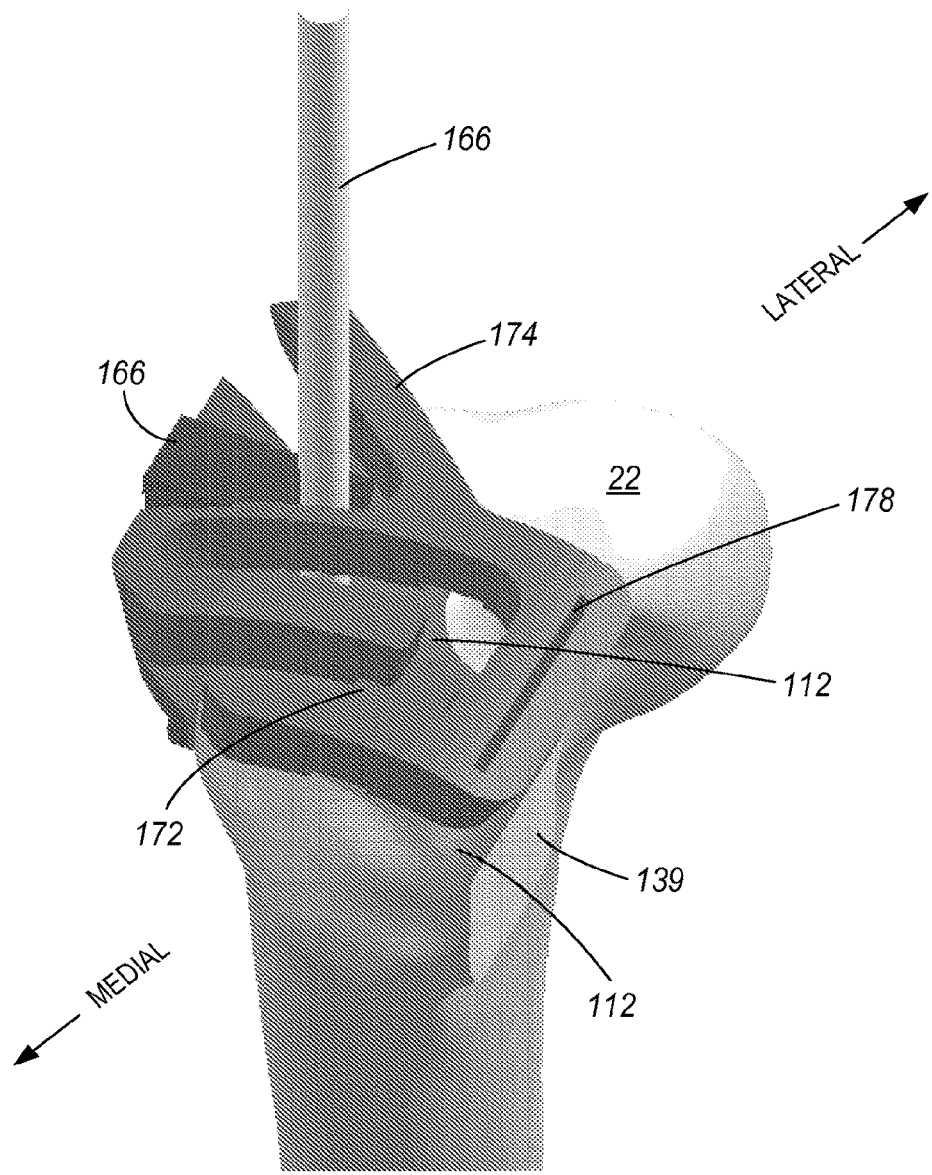

FIG. 37 is a perspective view of the guide of FIG. 33.

Figure 38:
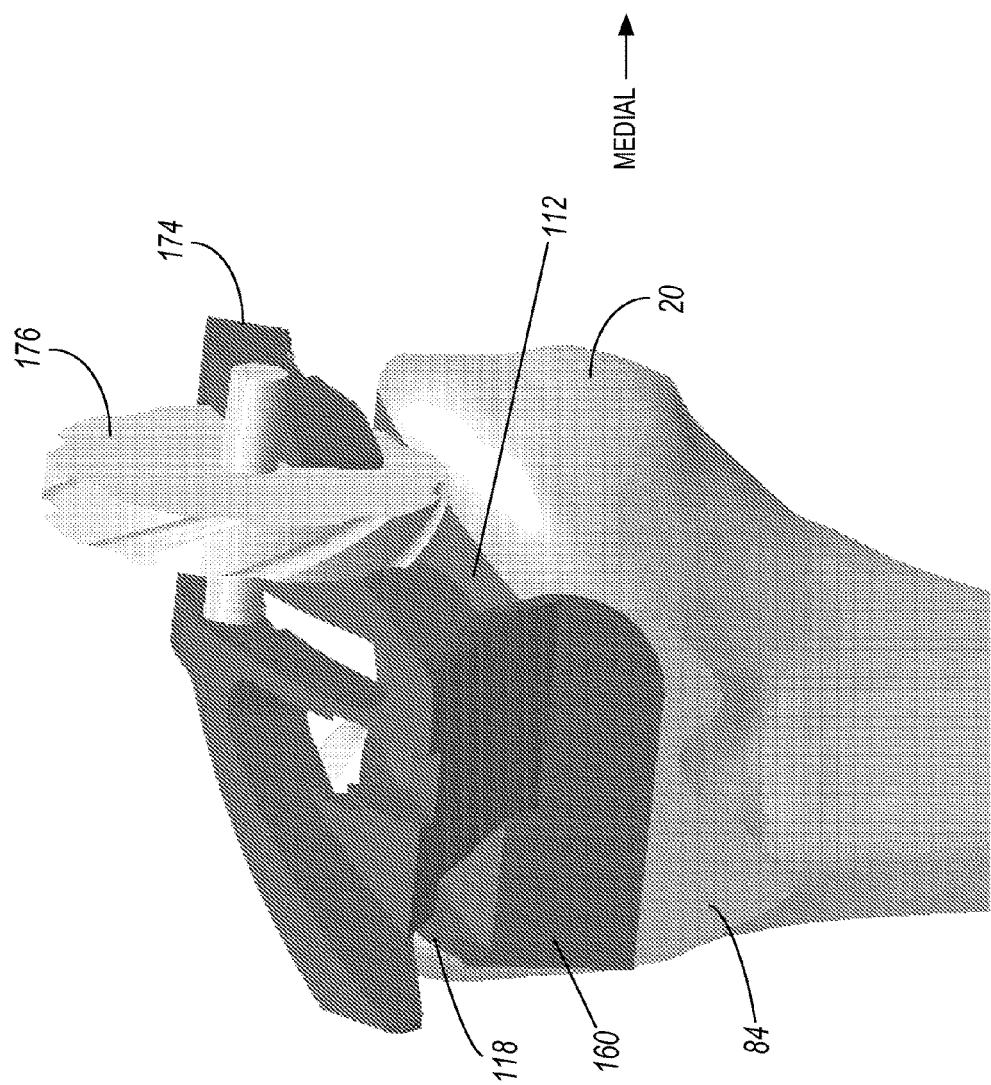

FIG. 38 is a perspective view of a milling guide used with a milling apparatus which rotates about a medial/lateral axis according to an alternate embodiment of the invention.

Figure 39:
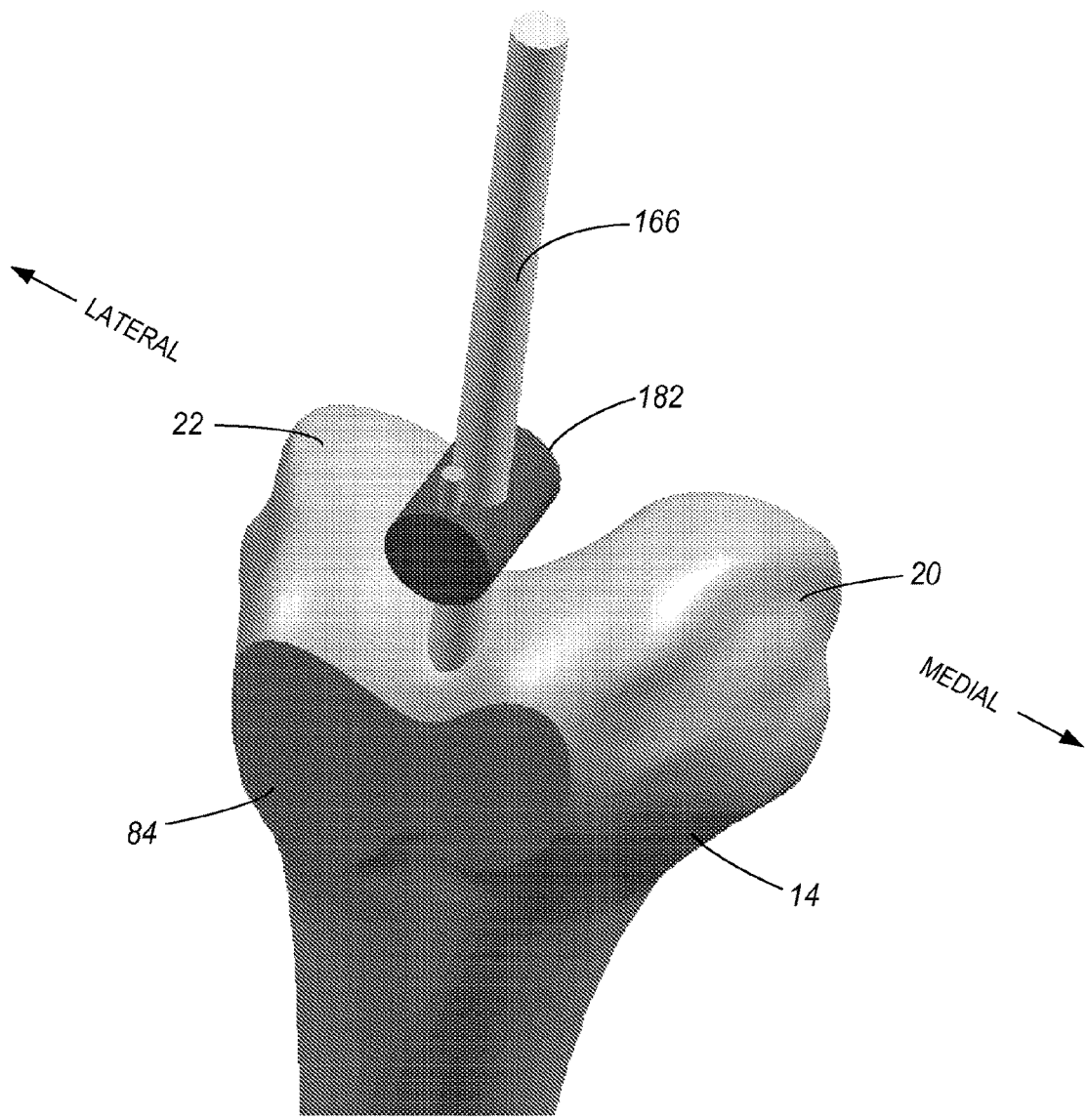

FIG. 39 is a perspective view of a collet 182 for use in connection with a guide 180 according to another alternate embodiment of the invention.

Figure 40B:
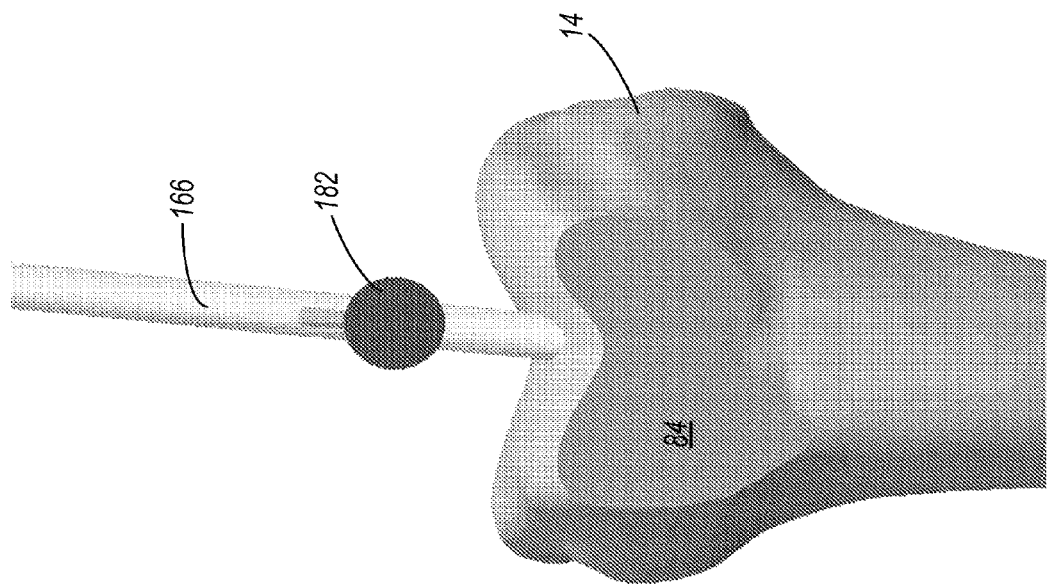
Figure 40A:
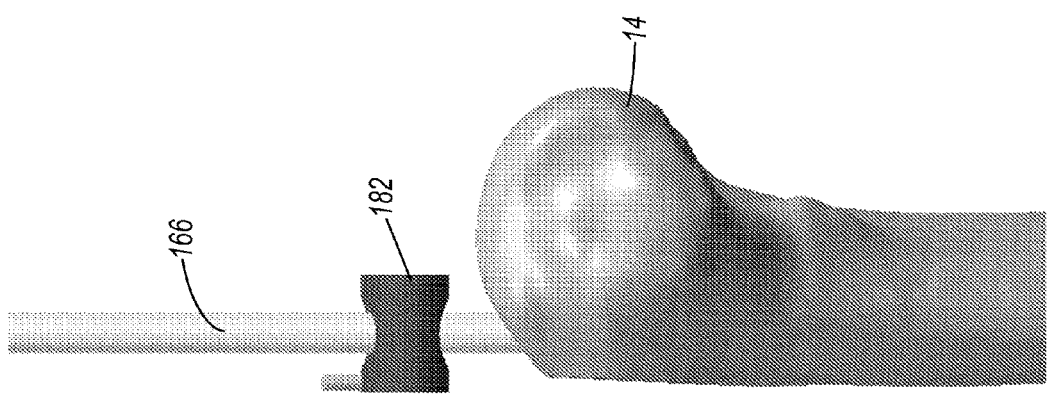

FIGS. 40 A and B are side and front views, respectively, of the collet of FIG. 39.

Figure 41:
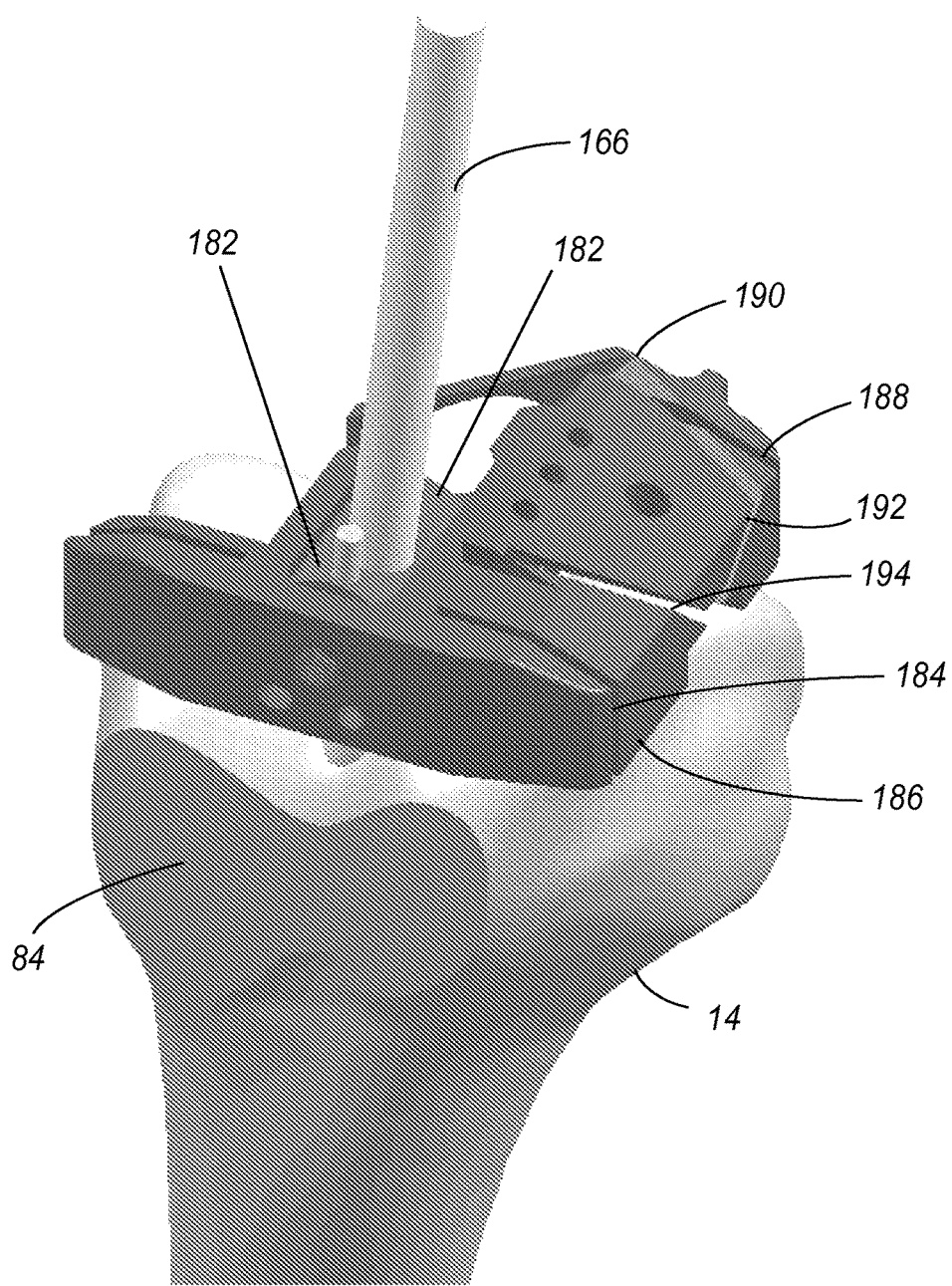

FIG. 41 is a perspective view of a resection guide according to another alternate embodiment of the invention.

FIG. 42A and FIG. 42B are side and front views, respectively, of the guide of FIG. 41.

Figure 43:
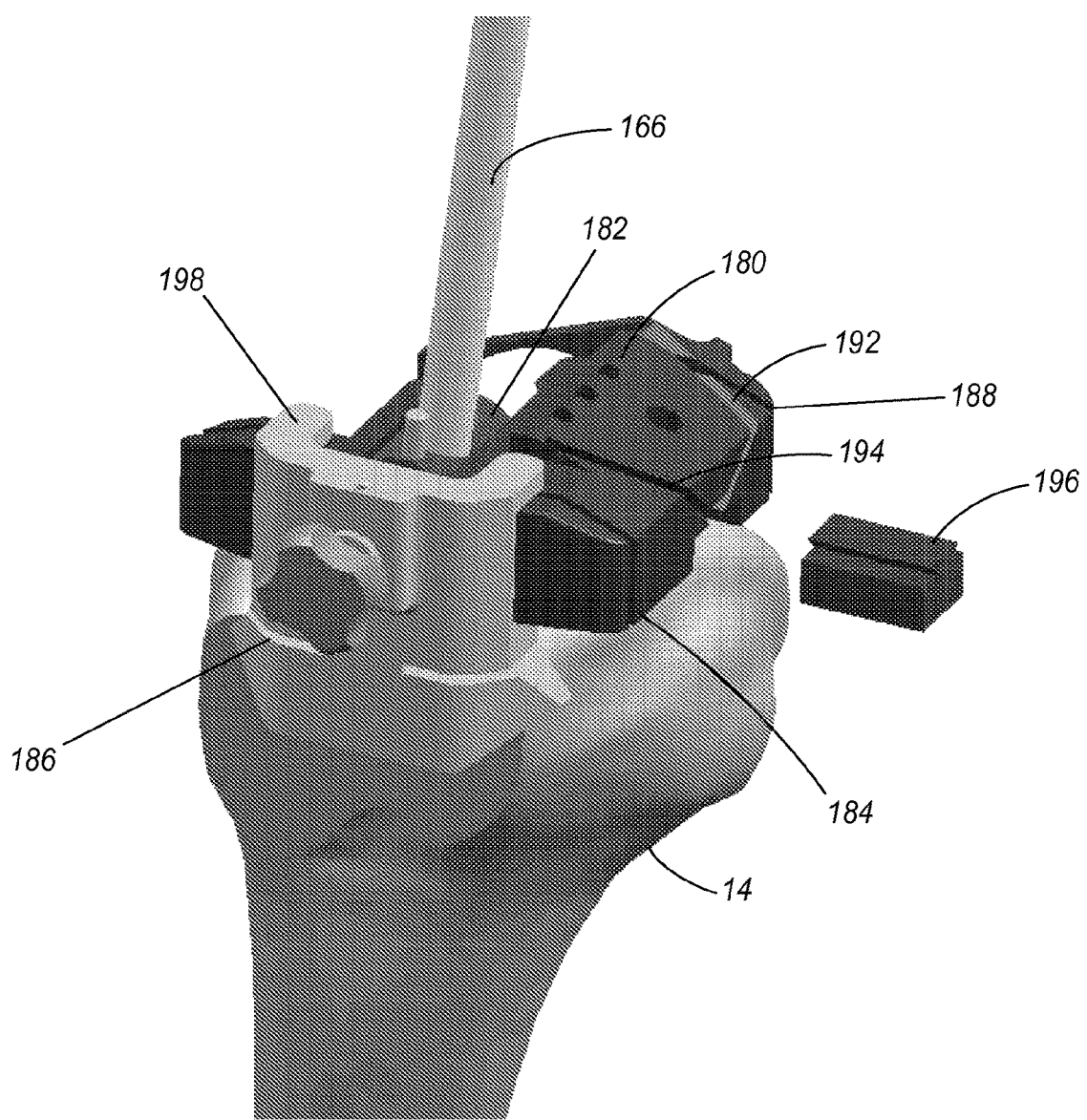

FIG. 43 is a perspective view of the guide of FIG. 41.

Figure 44B:
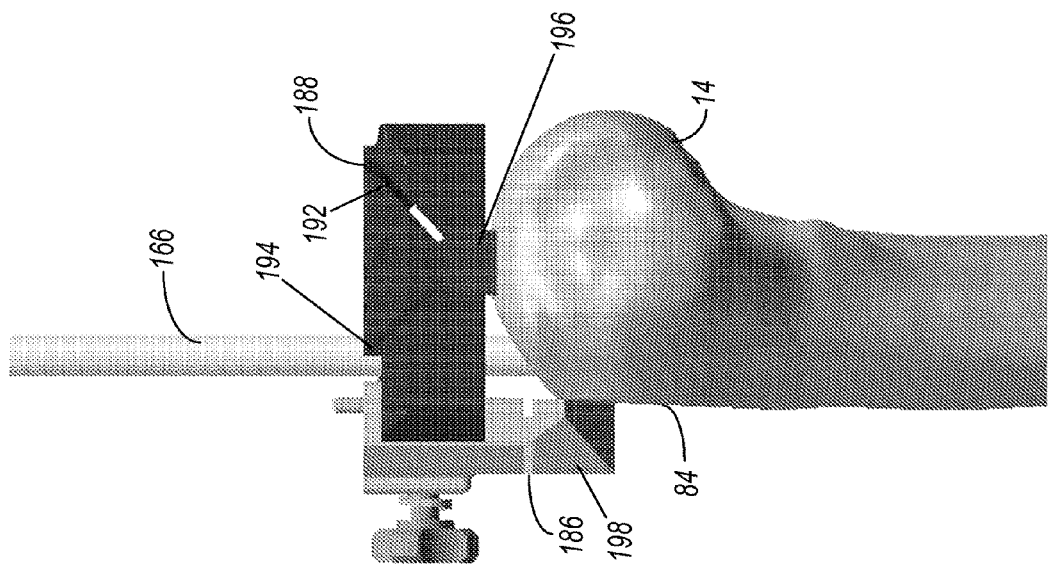
Figure 44A:
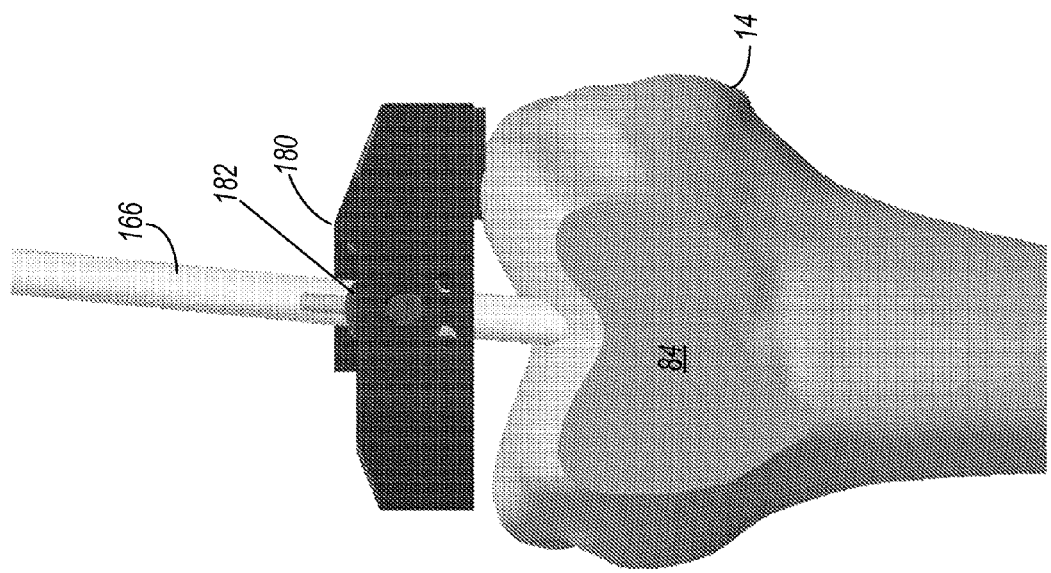

FIGS. 44A and 44B are front and side views of the guide of FIG. 41.

Figure 45:
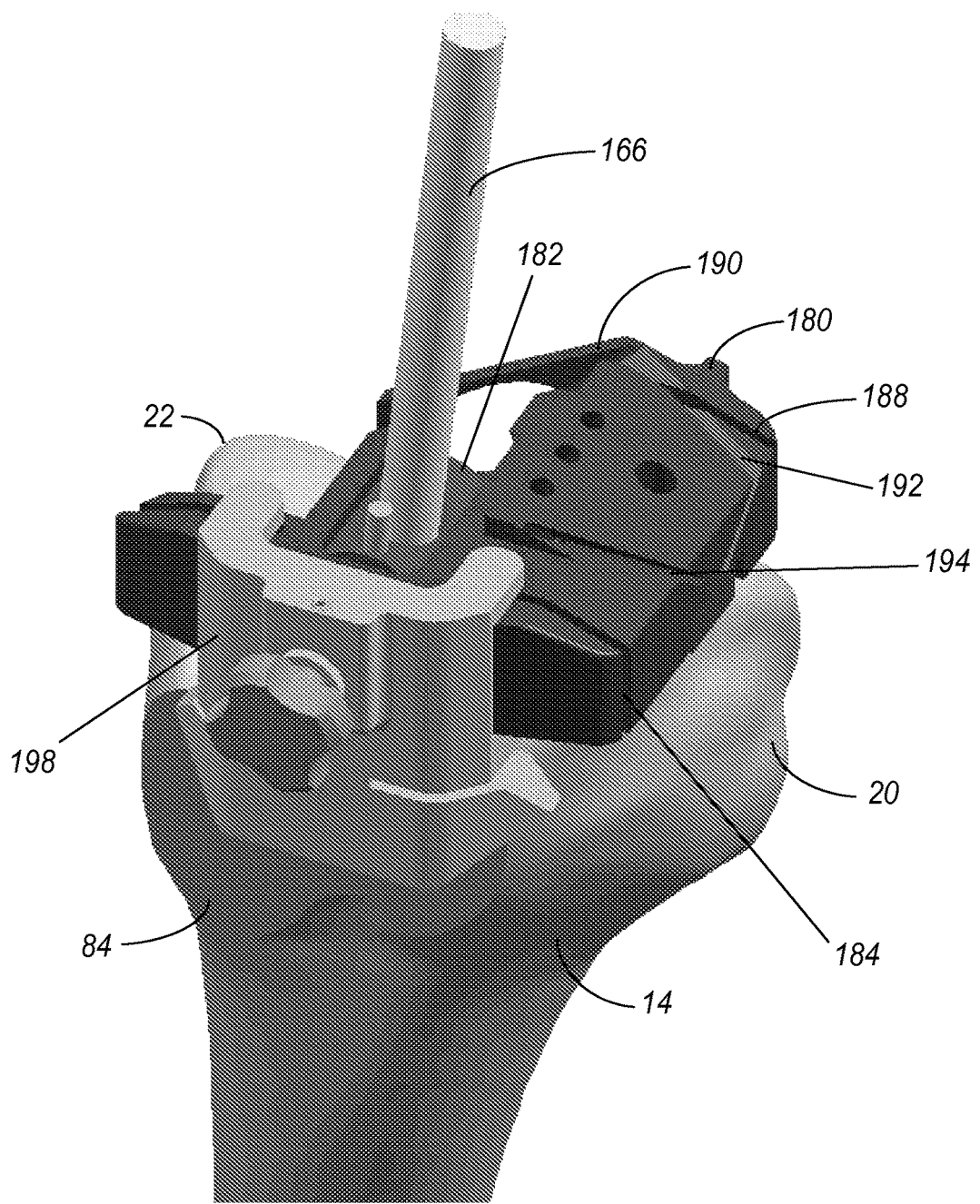

FIG. 45 is a perspective view of the guide of FIG. 41.

FIGS. 46A and 46B are front and side views of the guide of FIG. 41.

FIGS. 47A and 47B are side views of the guide of FIG. 41.

FIGS. 48A and 48B show the guide of FIG. 41 and a femur resected using the guide of FIG. 41.

FIGS. 49A and 49B show a femur resected using the guide of FIG. 41.

DETAILED DESCRIPTION

FIGS. 1 and 2A are front views of an implant 10 according to an embodiment of the invention. Implant 10 is adapted to be installed on the distal portion 12 of a human femur 14. The femur can be that of a human or other being with appropriate hinge joints. FIG. 2A shows an implant 10 placed on a sawbones model of a human femur 14. Anatomically, the femur 14 cooperates with the tibia 16 to form the knee joint 18. The distal portion 12 of the femur 14 includes two condyles, a medial condyle 20 and a lateral condyle 22. These condyles articulate (move in gross motion, whether rotational or translational or both) relative to the tibial plateau 24 which is a surface on the proximal portion 26 of tibia 16. Not shown is a patella which is connected to a patella tendon, also not shown, which in turn inserts on the tibia and attaches to the head of quadricep muscles to apply traction for extension of the knee joint. The patella tracks, as by sliding, in the patellofemoral channel 30. Patellofemoral channel 30 of implant 10 shown in FIG. 2A replicates the patellofemoral channel in the anatomical knee, which is a channel on anterior and distal surfaces of the femur between condyle 20 and lateral condyle 22 for tracking of the patella during flexion and extension of the knee 18. Ordinarily, the femur 14 and tibia 16 do not contact each other but instead each bear against menisci (not shown) which are interposed between condyles 20, 22 on the one hand and tibial plateau 24 on the other hand. An anterior cruciate ligament (not shown) and a posterior cruciate ligament (not shown) are among two of the ligaments which are connected to both the femur 14 and the tibia 16. One of the primary purposes of these ligaments is to control translation of the femur 14 and the tibia 16 relative to each other and in an anterior/posterior direction. These two ligaments in particular are important for knee stability and it is often preferred to preserve them if possible during knee surgery.

Figure 2C:
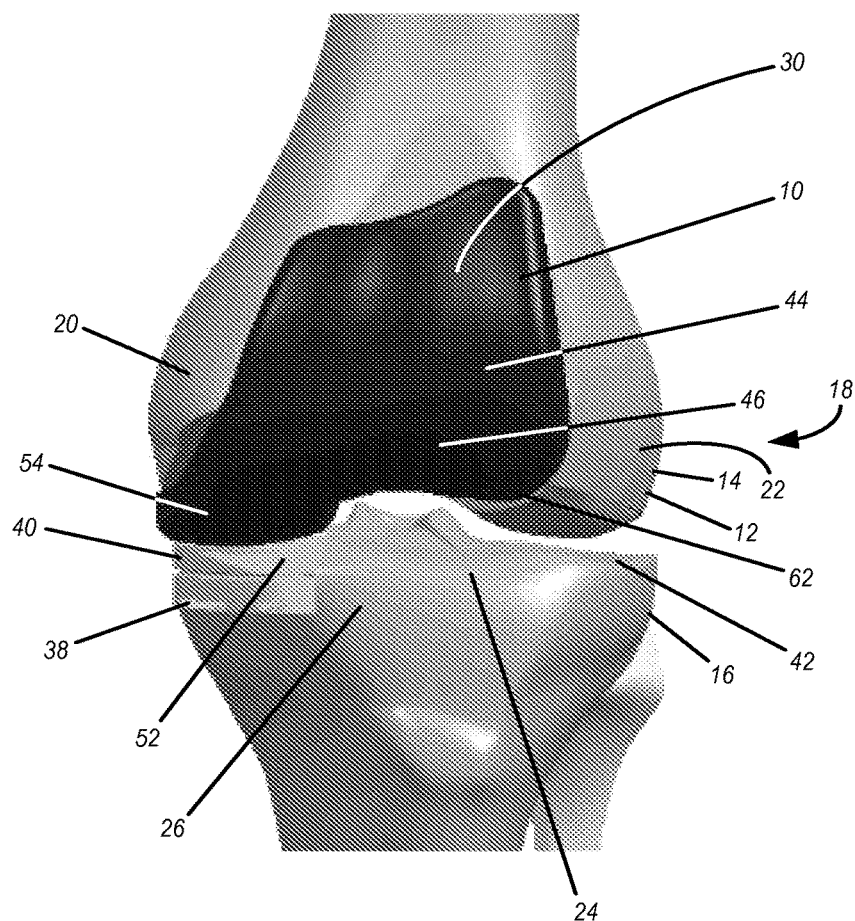
FIG. 2C is a front view corresponding generally to FIG. 2A with the knee shown in approximately full extension.

FIG. 2B is a navigational rose that corresponds to FIG. 2A. It shows the three degrees of translational freedom and the three degrees of rotational freedom that define the six degrees of potential freedom of motion in a knee such as the one shown in FIG. 2A. Translationally, the degrees of freedom are lateral/medial, anterior/posterior and superior/inferior. Rotationally, the degrees of freedom are flexion/extension, internal/external and varus/valgus. In that respect, FIGS. 2C AND 2D show a knee 18 with an implant 10 according to an embodiment of the invention installed on the femur with the knee at essentially zero degrees of flexion, and approximately 90 degrees of flexion, respectively.

FIG. 1 shows an implant 10 according to an embodiment of the invention together with a tibial implant 38 and a corresponding insert 40 which together form a prosthesis for reconstructing a portion of the knee 18. The implant 10 preferably does not replace some portions of the lateral condyle 22 that articulate against the menisci in the lateral compartment 42, and thus indirectly tibia 16. However, it does replace portions of the knee 18 such as those discussed above that are often found to be more prone to osteoarthritis—the portions of the medial condyle 20 that articulate against medial compartment menisci and thus indirectly against tibia 16 (for the prostheses installed) and the patellofemoral channel 30. Such a structure is beneficial for a number of reasons, including that the lateral compartment 42 of the knee 18 (which includes portions of the lateral condyle 22 and lateral portions of tibia 16) is preserved with multiple beneficial effects. In addition to improved kinematics and greater stability, such partial knee replacements can reduce contact of soft tissue connecting the femur 14 and the tibia 16 or lateral and medial sides of the knee with the implant 10, and thus lesser wear, particularly on the lateral side of knee 18. Additionally, the implant can be installed using minimally invasive surgical procedures to shorten the hospital stay, simplify the surgical procedure, and improve therapy prospects and long-term results, among other benefits. Furthermore, the implant can be installed without sacrificing the anterior cruciate ligament 34 and the posterior cruciate ligament 36 (not shown).

Implant 10 and tibial implant 38 may be made of conventional metallic or other materials conventionally used for knee prosthetics, including without limitation cobalt-chrome alloys, alloys which have been treated with zirconium oxide or other treatments, stainless steel materials and other metals or materials. Insert 40 may be formed of conventional ultra high molecular weight polyethylene of the sort conventionally used to form inserts in knee prosthetics, or it may be formed of any desired material.

Figure 2D:
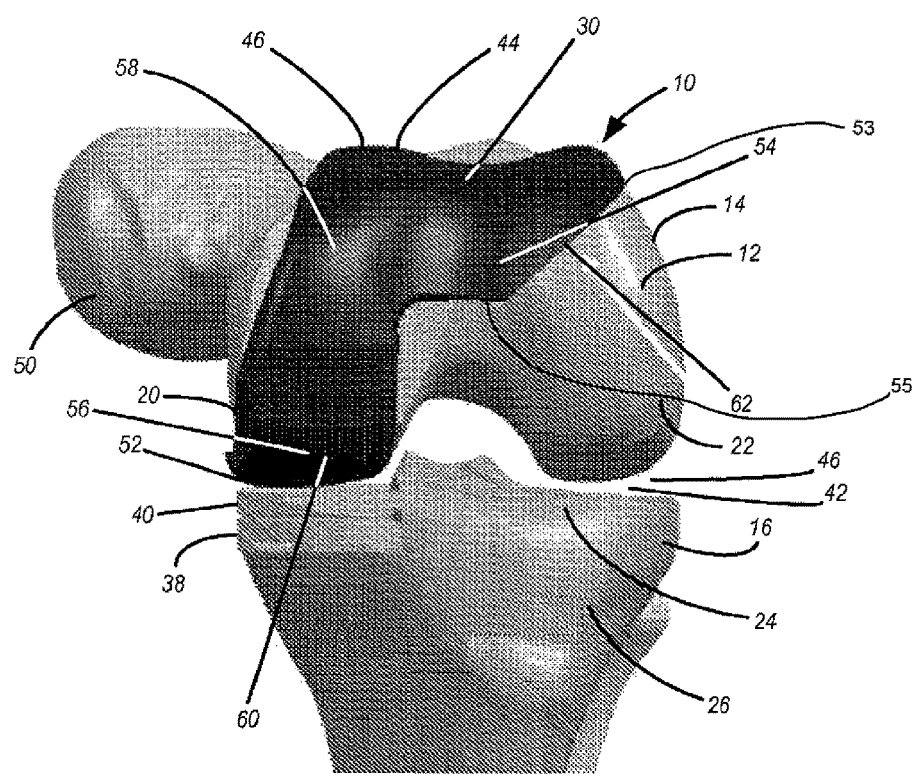
FIG. 2D is a front view of the knee of FIGS. 2A and C with the knee shown in approximately ninety degrees flexion.

FIG. 2D is a front view of the anterior portion of tibia 16 with knee 18 in approximate 90 degrees of flexion. The distal portion of femur 14 is evident, with lateral condyle 22 intact and the implant 10 replacing portions of the medial condyle 20 and the patellofemoral channel 30. (The femoral head 50, which forms part of the hip socket, can also be seen in this view and can give some degree of intuitive appreciation for why it may be that medial compartment 52 of the knee is sometimes more prone to osteoarthritis and other wear than is lateral compartment 42.)

As shown in FIG. 2D, distal portion 54 of implant 10 generally corresponds to the portion of the implant 10 between the anterior portion 44 and the posterior medial condylar portion 56 of implant 10. Anterior portion 44 includes distal edge 55 and lateral margin 53. It also corresponds generally to distal regions of the medial condyle 20 and patellofemoral channel 30 of the femur 14. On the medial side of the knee 18, portions of distal articulating surfaces 58 of implant 10 articulate against tibial insert 40 which itself is positioned relative to tibial implant 30 on proximal portions of the tibia 16 where the tibial implant 38 and insert 40 are used. (In circumstances where the tibial components are not used, distal articulating surfaces 58 of implant 10 can articulate against menisci and tibial plateau 24). On the lateral side of the knee, FIG. 2D makes evident a beneficial result of implant 10, that the lateral distal surfaces of the femur 14 and the tibia 16 remain in place to articulate relative to each other. According to this embodiment, the lateral compartment of the knee 42 is left in place so that the implant 10 does not articulate with the tibia 16 in that compartment. Rather, the transition 62, discussed below, between the implant 10 and the lateral articulating surfaces of the femur 14 is angled and is located sufficiently anterior on the lateral side of the femur 14 to reduce chances of such articulation, while yet providing sufficient replacement of portions of the patellofemoral channel 30 of the femur 16 which often suffer arthritic or other degradation when the medial condyle 20 does.

As shown in FIG. 2D, posterior medial articulating surfaces 60 of implant 10 articulate against insert 40 at greater degrees of knee 18 flexion. In circumstances where implant 38 and insert 40 are not used, the posterior medial articulating surfaces 60 articulate against menisci and thus tibia 16 indirectly.

FIG. 2D shows, on the lateral side of the knee 18, a transition portion of implant 10 of this disclosed embodiment of the invention which includes transition 62. The structure of this implant 10 aims to create a smooth transition from the natural bone lateral condyle 22 material to the implant 10 material. A transition 62 can be considered smooth if it does not suffer undue implant 10 or bone surface overhang or discontinuity between implant 10 and bone. Additionally, the transition 62 with its angled resection of bone does not require any resection of the anterior cruciate ligament or posterior cruciate ligament. The reasons for this include that resections required for implant 10 do not require cutting of those tissues during minimally invasive surgery or otherwise, and that no portions of the implant 10 interfere with those tissues when the implant 10 is inserted into the knee 18 and positioned on the femur 14 during minimally invasive surgery. Other advantages of the structure and shape of implant 10 are evident to a person of ordinary skill in the art from FIG. 2D (as well as other figures and other portions of this document) and bearing in mind how the implant 10 is installed during surgical procedure. Additionally, as mentioned above, the transition 62 feature provides an implant 10 structure where the lateral meniscus preferably does not come into contact with the femoral implant, but rather articulates preferably only against natural bone of the lateral condyle 22.

Accordingly, FIG. 2D shows a distal view of a femoral implant which differs from implants such as conventional implants used in bicompartmental knee arthroplasty, because (among other things) it omits lateral condylar distal and proximal portions and instead truncates the lateral structure with transition 62.

Figure 2E:
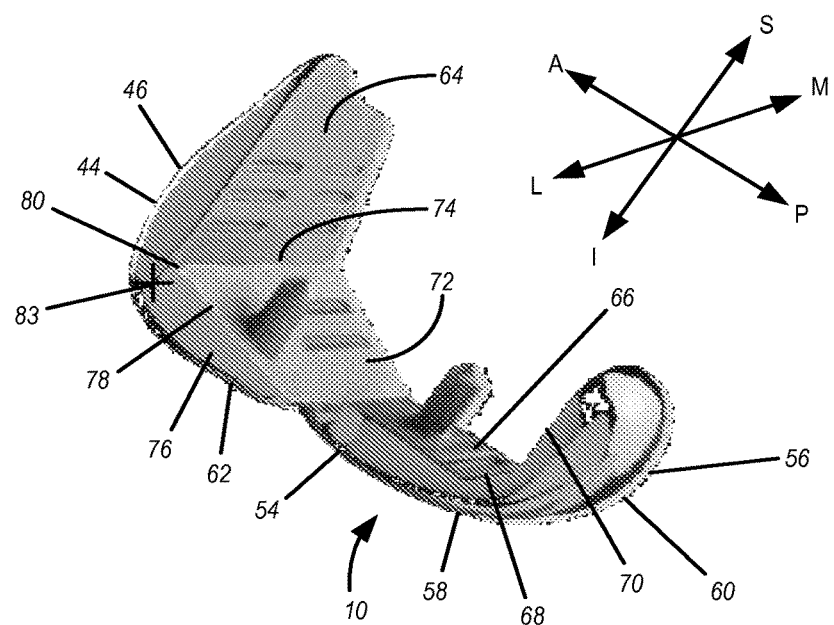
FIG. 2E is a perspective lateral view of an implant according to one embodiment of the invention made for a left knee.

FIG. 2E shows a perspective view of the implant 10 of FIG. 1 from another perspective which is helpful in understanding the transition 62 and other geometric and navigational aspects and features of certain embodiments of the invention. Among other things, the inner surfaces of the implant 10 are shaped and oriented in a manner that allows precise and accurate positioning of implant 10 on femur 14 in order, among other things, to replicate motion of the natural knee and optimize the benefits of maintaining natural bone in the lateral condyle 22 using transition 62 or similar constructs and related geometry and structures, while producing a smooth transition from bone to implant across transition 62.

FIG. 2E shows a navigational rose which is helpful in understanding the orientation of various surfaces of implant 10. Anterior articulating surfaces 46, distal articulating surfaces 58 and posterior medial articulating surfaces 60 are evident. A transition portion of implant 10 including transition 62 is also evident. A number of surfaces are shown in FIG. 2E as cooperating to form inner surfaces of implant 10. As is known to those who design and install femoral implants, these surfaces are formed with a view to fitting to distal areas of the femur 14 which have been resected to correspond to the surfaces. Some or all of the surfaces may be cemented to the bone or may contain bone in-growth material such as sintered beads or wires or other porous or similar material which enhances growth of bone into the surface of the implant, or they may feature any desired surface characteristics. In the particular implant shown in FIG. 2E, all of these surfaces on the inner side of implant 10 are substantially planar, that is generally flat in the shape of a plane but including the possibility of discontinuities such as bone ingrowth material, indentations, raised areas, pegs, openings and other surface discontinuities which could otherwise technically be said to remove a surface from the strict category of being substantially in a plane or being planar. However, implants according to the invention can also feature one or more interior surfaces which are curved, to fit resected surfaces which have been formed by resection guides of the present invention that resect curved surfaces onto bone as by using milling, grinding, routing, machining, or similar apparatus which is capable of forming curved surfaces on materials (hereinafter "milling" devices or apparatus).

In the particular implant 10 shown in FIG. 2E, anterior inner surface 64, distal inner surface 66, posterior chamfer surface 68 and posterior inner surface 70 are intended substantially to abut corresponding portions of resected bone or shims or inserts which are interposed between bone and implant to compensate for undue bone loss or for other reasons. Anterior inner chamfer surface 72 is disposed between distal inner surface 66 and anterior inner surface 64 to intersect, preferably as a line, anterior intersection line 74.

Additionally, transition surface 76 which is also preferably but not necessarily substantially planar, extends along lateral portions of implant 10 to intersect anterior inner chamfer surface 72, preferably in a line, the lateral intersection line 78. In this particular structure of this embodiment of the invention shown in HG. 2E, the anterior inner surface 64, anterior inner chamfer surface 72, and transition surface 76 intersect at a point on lateral portions of the implant 10, the convergence point 80. As a corollary in this construct, anterior intersection line 74 and lateral intersection line 78 intersect at convergence point 80. In a similar fashion, planes of the anterior inner surface 64, transition surface 76 and distal inner surface 66 intersect at implant point 83.

Implant point 83 in some embodiments is located laterally, when the implant 10 is installed on femur 14, to transition point 82.

In the particular implant shown in FIG. 2E, transition surface 76, like other inner surfaces, is planar, although it can be curved in other implants according to other embodiments of the invention. A primary aim of some embodiments of the invention is to define and use a reference or navigation point on the bone for positioning and orienting resections and therefore implant 10. So long as a navigational point such as a transition point on the bone can be designated to properly form resections that will permit an implant to be properly positioned and oriented on the femur for good knee kinematics and performance, the particular shape of the resected surfaces and corresponding implant surfaces, whether curved or planar, and how the resections are formed, whether by sawing, milling or otherwise, matter less and can be accommodated within the principles of the invention.

Figure 3:
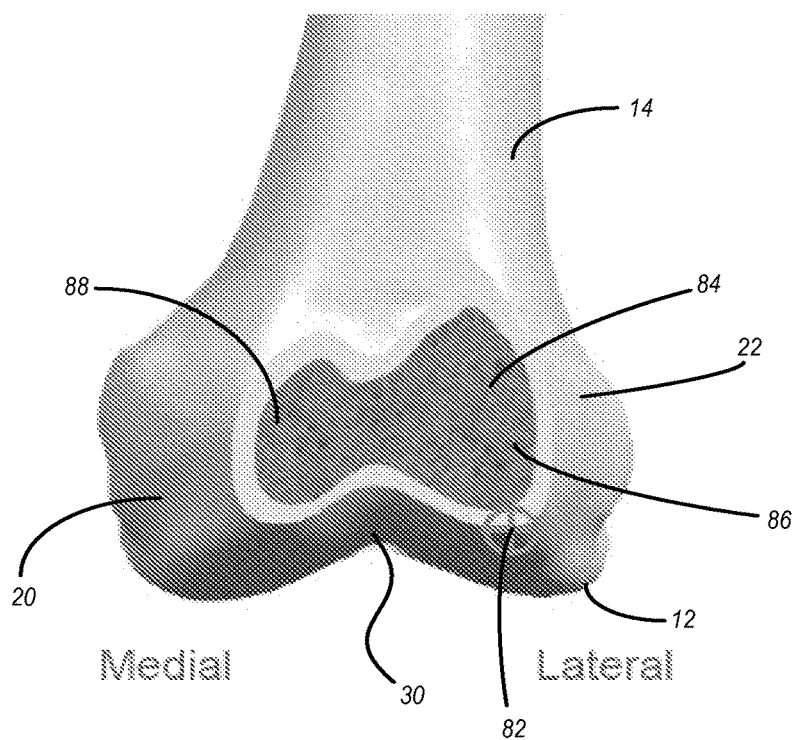
FIG. 3 is a front view of a human femur on which has been performed an anterior resection according to one embodiment of the invention.

FIG. 3 is a front view of distal portions of a femur 14 which shows an anterior resection 84 and a transition point 82 designated on the bone that can be used to position and orient a distal resection 100 (discussed below) of the femur 14 that, in combination with the anterior resection, ultimately allow positioning of an implant such as shown in FIGS. 1 and 2 on the bone. Accordingly, among other things, the implant can be located and oriented properly relative to mechanical axes of the anatomy and otherwise for proper flexion/extension and other kinematics and functioning of the knee, and also to allow the transition from bone to implant 10 across transition 62 to be smooth, so that for instance it suffers minimal discontinuities such as overhang of implant or bone.

In the femur 14 shown in FIG. 3, anterior portions of the femur 14 have been resected to form anterior resection 84 using instrumentation that corresponds to the implant shown in FIGS. 1 and 2, as discussed more fully below. Anterior resection 84 will correspond to anterior portion inner surface 64 of implant 10 when the implant 10 is installed on femur 14. Anterior resection 84 is often hourglass in shape with a lateral lobe 86 and a medial lobe 88. The transition point 82 can be chosen as the distal-most point of lateral portions of anterior resection 84, which in the drawing of FIG. 3 is the distal-most point on the lateral lobe 86 of anterior resection 84. What point is distal-most for purposes of determining the location of the transition point 82 on the bone can be considered as intersection of a line that is parallel to a line connecting distal-most portions of the medial and lateral condyles 20, 22.

Alternatively, location of transition point 82 can be at another location inside or outside of anterior resection, or at any other desired point on the bone. What matters primarily is anterior resection 84 be formed properly on the femur 14 in the anterior/posterior dimension and in internal/external rotation (see FIGS. 6A-6F) and that a transition point can be designated relative to which a distal resection 100 (discussed below) can be formed properly in the superior/inferior dimension relative to the anterior resection 84 and oriented properly in varus/valgus rotation. Proper positioning of an implant 10 with corresponding surfaces can then be achieved so that among other things, the implant can be located and oriented properly relative to mechanical axes of the anatomy and otherwise for proper flexion/extension and other kinematics and functioning of the knee, and also to allow the transition from bone to implant 10 across transition 62 to be smooth, so that for instance it suffers minimal discontinuities such as overhang of implant or bone.

Figure 4:
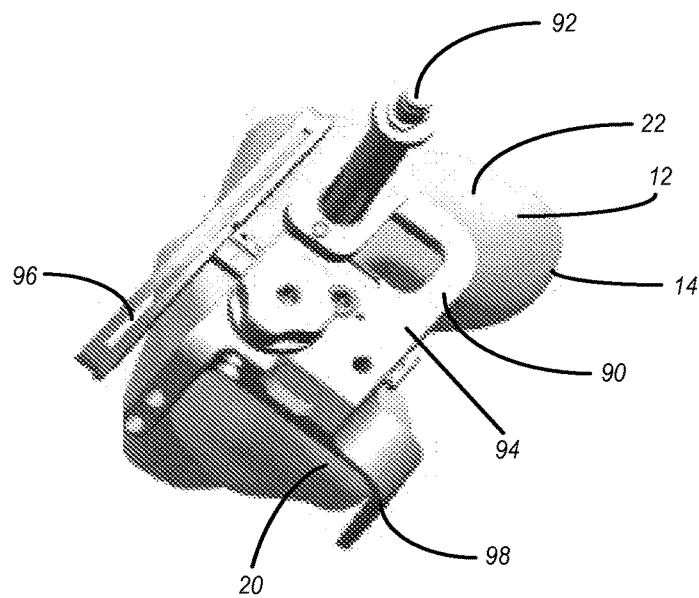
FIG. 4 is a perspective view of an anterior resection guide according to one embodiment of the invention in place on a patient's femur to perform an anterior resection such as shown in FIG. 3.
Figure 5:
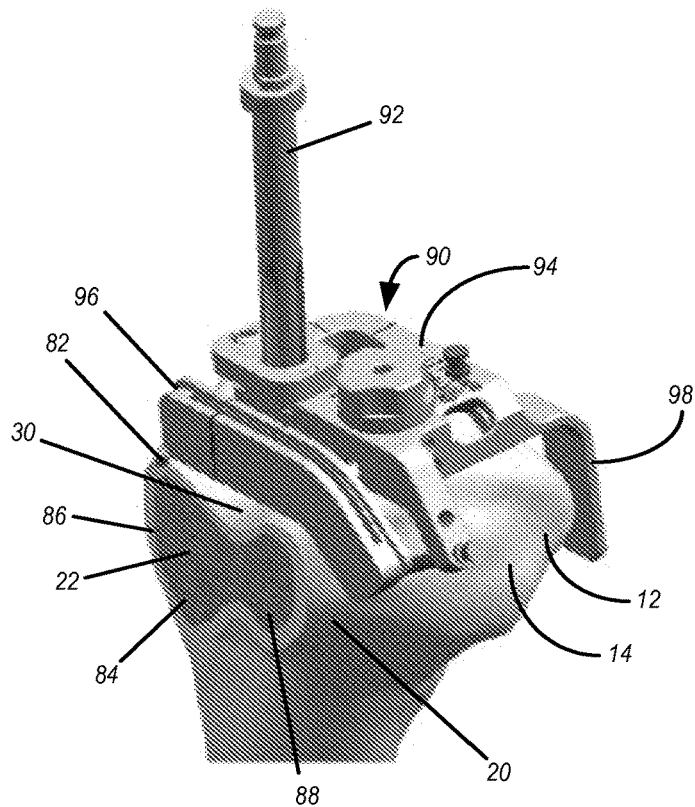
FIG. 5 is a perspective view of the anterior resection guide of FIG. 4 in place where the anterior resection has been performed.

FIG. 4 shows an anterior resection instrument 90 according to one embodiment of the invention for performing an anterior resection 84 on femur 14 to accommodate the implant 10 of FIGS. 1 and 2. Instrument 90 is coupled to an intramedullary rod 92 which has been inserted into the distal portion 12 of femur 14. An extramedullary rod can be used instead of the intramedullary rod. Before instrument 90 is coupled to intramedullary rod 92, a template or other device may be employed to mark geometry on the femur 14, such as the anterior-posterior line and/or a line perpendicular to it. The instrument 90 may be coupled to the intramedullary rod and aligned with such indicia to ensure that anterior resection 84 is properly oriented and located. The instrument 90 shown in FIGS. 4 and 5 includes a body 94 to which may be connected in sliding fashion for adjustment in the anterior-posterior direction, an anterior resection guide surface 96. Body 94 may be connected to intramedullary rod 92 or extramedullary rod with a collar or other desired structure to allow for translational and/or rotational freedom as desired. In the embodiment shown in FIG. 4, body 94 can be controllably constrained from rotating in any direction relative to the rod, although the rod itself may be rotated in bone to align the body 94 with the indicia marked on the femur 14. However, body 94 can move in the anterior-posterior direction relative to the rod, and the guide surface 96 can move relative to body 94 in the same direction. Body 94 is also able to slide relative to the rod in the superior/inferior direction. In the particular embodiment shown in FIGS. 4 and 5, the body 94 is constrained from translating in the medial/lateral direction, although that need not necessarily be the case. A paddle 98, with or without other components connected to body 94, can be used to determine the appropriate size of implant 10 and thus, in some aspects of the invention, in some cases, size of certain instrumentation which will be used to install the implant 10. Once the instrument 90 and particularly body 94 and anterior resection guide surface 96 have been properly positioned, guide surface 96 may be used to create anterior resection 84.

FIGS. 6A-F show effects of moving the guide surface 96 in the anterior-posterior direction to perform the anterior resection 84. FIGS. 6A and 6B show an anterior resection 84 made with the guide surface 96 position in a "neutral" anterior-posterior position. If the guide surface 96 is positioned posteriorly to that "neutral" position, FIG. 6D shows how the shape and size of anterior resection 84 changes and enlarges, respectively. If the guide surface 96 is positioned more anterior to the "neutral" position, FIG. 6F shows that the anterior resection 84 diminishes in size and changes shape. Although the shape of each of the particular anterior resections 84 shown in FIGS. 6B, 6D and 6F are hourglass and feature lateral lobes 86 and medial lobes 88, it is possible that at some point the shape could be other than hourglass such as if the guide surface 96 is positioned sufficiently posterior of the "neutral" position to make it more heart shaped, or if it is positioned sufficiently anterior of the "neutral" position to cause the anterior section 84 to take the form of two ovals or other rounded closed areas.

FIGS. 7A-F show effects of internal and external rotation of the guide surface 96 relative to intramedullary or extramedullary rod 92 to perform the resection. FIG. 7B shows the anterior resection 84 formed when the guide surface 96 is positioned in a neutral internal-external rotational orientation. FIG. 7D shows the anterior resection 84 when the guide surface 96 has been positioned with two degrees of internal rotation relative to intramedullary rod 92. The size of the lateral lobe 86 has diminished and the size the medial lobe 88 has increased. As shown in FIG. 7F, two degrees of external rotation of the guide surface 96 relative to intramedullary rod 92 to form the anterior resection 84 causes the opposite effect: the lateral lobe 86 increases in size and the medial lobe 88 decreases in size.

FIGS. 6 and 7 show that positioning of the anterior resection guide surface 96 and the anterior-posterior translational and the internal-external rotational direction can change the size and shape of the anterior resection 84 and therefore in some embodiments the location of the bone transition point 82 that is employed to create the right distal resection 100/anterior resection 84 location and orientation to allow proper positioning of implant 10 as shown in FIGS. 1 and 2.

Figure 8A:
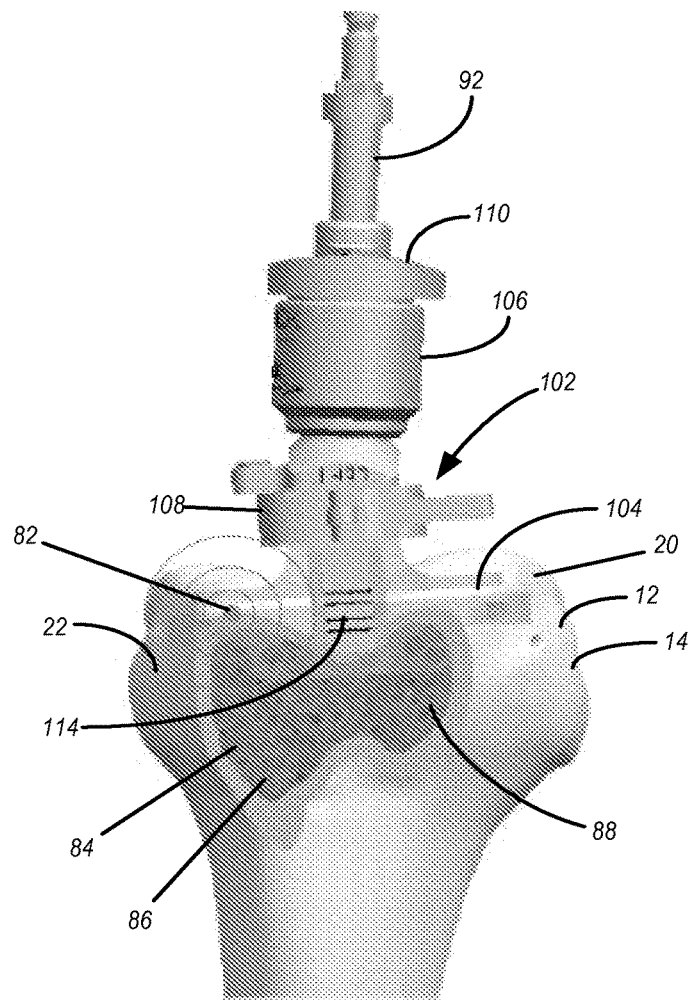
FIG. 8A is a front view of a distal resection guide according to one embodiment of the invention in place on a human femur, to perform a distal resection on the medial condyle according to one embodiment of the invention.
Figure 8B:
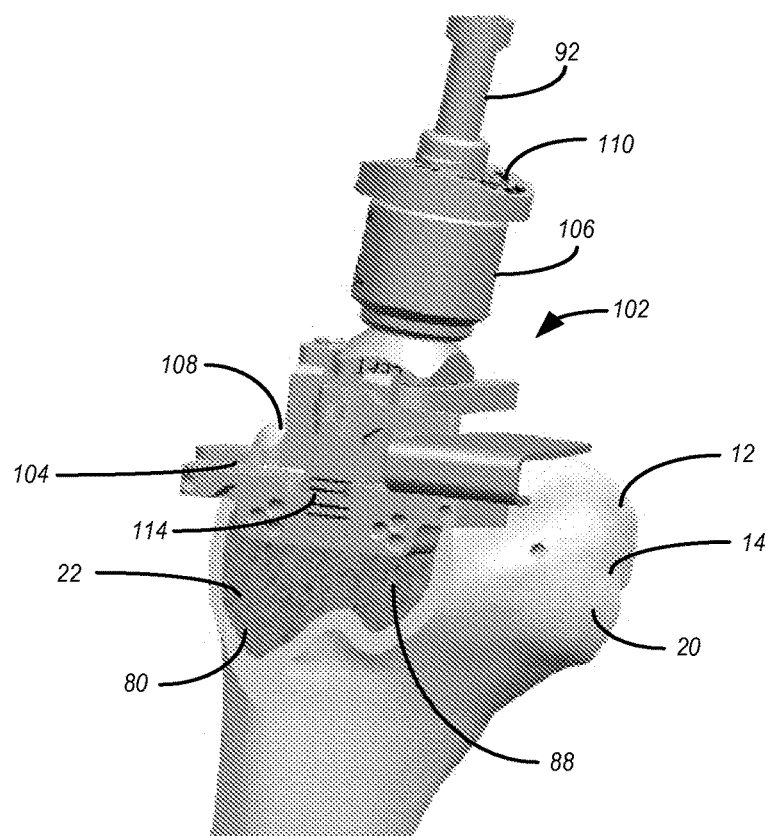
FIG. 8B is a front view of a distal resection guide according to one embodiment of the invention in place on a human femur, with a shim, to perform a distal resection on the medial condyle according to one embodiment of the invention.

After the anterior resection 84 has been performed using this particular embodiment of the invention, instrument 90 may be removed from the intramedullary rod 92 and a distal resection instrument 102 coupled to that intramedullary rod 92 for performing a distal resection 100 on the medial condyle of the femur 14. FIGS. 8A and 8B show one such distal resection instrument 102 according to this embodiment of the invention.

Distal resection instrument 102 shown in FIGS. 8A and 8B includes a distal resection guide surface 104 and structure for connecting it to the intramedullary rod 92. Preferably, that structure allows distal resection guide 104 to be adjusted in at least varus/valgus rotational and superior/inferior translational directions relative to the rod 92. The structure connecting the distal resection guide surface 104 and the intramedullary rod 92 can include, for example, a collet 106 and a body 108. The collet 106 can be positioned on the intramedullary rod 92 in sliding relationship and connected directly or indirectly to body 108 which can be connected directly or indirectly to resection guide surface 104. For example, guide surface 104 can be connected in sliding relationship to body 108 so that it can move relative to body 108 in anterior/posterior direction but be constrained in the other degrees of freedom with respect to body 108. Collet 106 can include indicia to select and/or indicate magnitude of rotation of guide 104 in the varus/valgus direction. One form of such indicia 110 can be seen on the top surface of collet 106 and FIG. 8B. Alternately, a series of collets can be provided for selection by the surgeon to accommodate various angles of varus/valgus. Distal resection guide surface 104 can also contain a plurality of openings 112 to receive pins for pinning it to the bone when properly positioned, for example by pinning it to the anterior resection 84.

A distal resection 100 can be performed on the medial condyle 20 such as by using instrument 102 as follows. Other instrumentation can also be used, and can suffice if it allows a distal resection to be made to the medial condyle 20 which substantially passes through or is navigated relative to transition point 82 and is correctly oriented in the varus/valgus direction. With reference to FIGS. 8A and 8B, distal resection instrument 102 can be placed on intramedullary rod 92 and positioned by sliding so that body 108 is positioned correctly to locate distal resection guide surface 104 so that it can be positioned and oriented relative to the bone transition point 82 and rotated in varus/valgus so that a distal resection 100 may be made using resection guide surface 104 which passes through, near or suitably relative to, transition point 80 and is properly oriented in varus/valgus. It may be desirable to position the resection guide surface 104 so that the distal resection 100 can pass proximal to the transition point 82 or, if desired, distal to it. Once the distal resection guide surface 104 has been properly positioned relative to intramedullary, extramedullary or other rod 92, it can be pinned to anterior resection 84, if desired, to perform the distal resection 100. Accordingly, the rod 92, body 108 and collet 106 can be removed from the bone to leave distal resection guide surface 104 retained in place by the pins. Resection can also be performed without pins if desired, by relying on rod 92 and the other structure of instrumentation 102 to retain the resection guide surface 104 in place while resection 100 is being performed.

To serve as a distal resection guide surface 104 index 114, a portion of the flat surface of the resection guide surface 104 can be employed to visually align the distal resection guide surface 104 with the transition point 82, or to place this portion of the resection guide surface 104 near, such as proximal or distal relative to, the transition point 82 so that distal resection 100 will pass through, near or suitably relative to, transition point 82. Alternatively, index 114 can include a physical indicium (not shown) such as a mark, engraving, raised portion, or other desired indicium on any portion of the distal resection guide surface 104.

After the distal resection 100 has been performed, distal resection guide surface 104 can removed from the bone (as can instrumentation 102 and intramedullary rod 92 if they were left in place).

Figure 9:
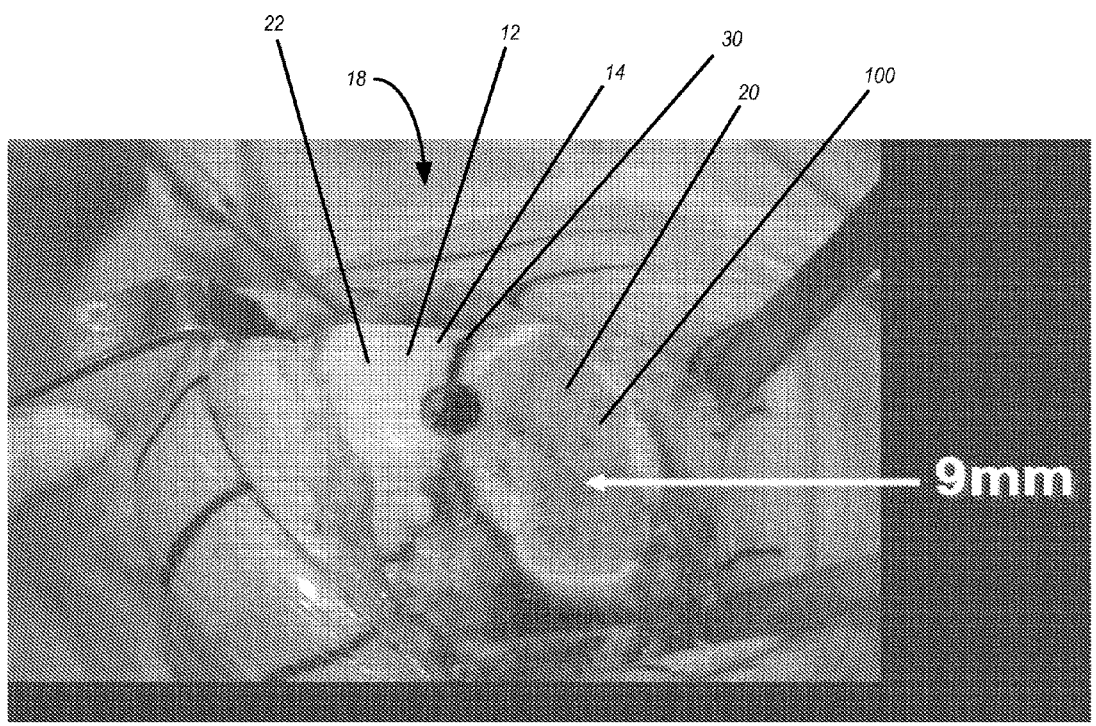
FIG. 9 is a front view of a human knee, with the femur in approximately ninety degrees flexion, showing the distal part of the femur after a distal resection to the medial condyle according to one embodiment of the invention has been made.

FIG. 9 shows a distal view of a distal resection 100 of the medial condyle 20 of a femur 14 performed using instrumentation as shown in FIGS. 8A and 8B. At this stage, after the distal resection 100 has been performed, the position and orientation of an implant 10 have been defined in at least four degrees of freedom by resecting in accordance with certain embodiments of the invention as disclosed above:

anterior/posterior translation as defined by the anterior resection 84;

superior/inferior translation as defined by the distal resection 100;

internal/external rotation as defined by the anterior resection 84; and varus/valgus rotation as defined by the distal resection 100.

Thus, essentially all that remains for determining proper location and orientation of the implant 10 on the femur 14 is medial/lateral positioning on the anterior resection 84 and distal resection 100.

For such medial/lateral positioning, a transition resection guide 116 according to an embodiment of the invention as shown in FIGS. 10-13, or other desired instrument, can be used. Among other things, the resection guide 116 shown in those FIGs. can be used to create transition resection 118 and anterior chamfer resection 120. Essentially, any structure is sufficient to perform these resections if a transition resection 118 can be performed using the instrumentation which positions properly the transition surface 76 of implant 10 or other implant according to the invention with reference to location and orientation of both anterior resection 84 and distal resection 100.

Resection guide 116 as shown in FIGS. 10-13 can include a finger or other index 122 for aligning guide 116 with transition point 82. Index 122 can correspond to a relevant landmark on the implant 10, such as a lateral outer extremity of the implant 10, or with a predetermined lateral/medial and/or superior/inferior offset distance, to a point located relative to the implant point 81. The index 122 may be of any particular structure or shape, including virtual if desired rather than physical. It can be connected to body 124 of resection guide 116 as by a flange 126 which has, on its posterior side as seen best in FIG. 13, an anterior resection alignment surface 128. Anterior resection alignment surface 128 can be used to position resection guide 116 as by positioning alignment surface 128 flat against anterior resection 84.

The body 124 or any other desired portion of resection guide 116 can include a distal resection alignment surface 130 which can be used to position resection guide 116 as by positioning it flat against distal resection 100. Resection guide 116 may thus be positioned against the femur 14 for proper resection of transition resection 118 and chamfer resection 120 by moving anterior resection alignment surface 128 on anterior resection 84 and distal resection alignment surface 130 on distal resection 112 while aligning or positioning index 122 medially or laterally to position transition resection guide 134 properly for a smooth transition of bone to implant across transition 62 which, for instance, features minimal discontinuities such as overhang of implant or bone. One way to achieve that result using the guide 116 shown in FIGS. 10-12 is to position index 122 laterally/medially to an extent that shows the surgeon where the lateral extremity of the implant 10 will be positioned relative to the bone, if a transition resection 120 is performed using transition resection guide surface 134 on guide 116 with guide 116 in that position. Condyle marks 125 on posterior surfaces of guide 116 (see FIG. 12) corresponding, for example, to condyle width, can also be used in combination with the index 122 for this purpose. Marks 125 or index 122 may be used independently, or guide 116 can include any other marks or indices for helping the surgeon determine where best to position the guide 116 and thus implant 10 laterally/medially for performing the transition resection 118 at a location that causes minimal surface discontinuity across transition 62 between implant 10 and bone.

Transition resection guide 116 can also contain a chamfer resection guide surface 132 for forming an anterior chamfer surface on the bone corresponding to chamfer surface 72 of the implant 10 (see FIG. 2E) and a drill guide bore 136 that is tangent to chamfer resection guide surface 132 and transition resection guide surface 134, or otherwise corresponds to their intersection. Guide 116 can if desired include a drill guide bore 136 which can operate as follows: Once the resection guide 116 has been properly positioned on the femur 14 as disclosed above, a drill may be aligned through drill guide bore 136 to form a bore 138 in the bone of the femur 14 that will correspond to lateral intersection 78 on the inner surface of implant 10 that extends from convergence point 80 in an angular fashion to help form the intersection between transition surface 76 of the implant and anterior inner chamfer surface 72 of implant 10 (see FIG. 2E). Transition resection 118 can then be performed using transition resection guide surface 134, and chamfer resection 120 can then be performed using chamfer resection guide surface 132. These resections can be performed without using drill guide bore 136 to form a bore 138, and drill guide bore 136 can be omitted from guide 116 if desired.

Anterior/posterior resection guide 116 may also include a posterior resection guide surface 137 for forming a posterior resection 139 that corresponds to posterior inner surface 70 of the implant 10. Similarly, resection guide 116 can include a posterior chamfer resection guide surface 140 for forming a posterior chamfer resection 142 on the bone that corresponds to posterior chamfer inner surface 68 of implant 10. These latter resections are shown in FIG. 13.

FIGS. 14-16 show an alternative form of resection instrumentation 144 which uses a single instrument 144 for performing both a anterior resection 84 and the distal resection 100. Anterior resection guide surface 147 can be used to perform an anterior resection 100 after instrument 144 has been adjusted so that anterior resection guide surface 147 is properly located in the anterior/posterior dimension and in internal/external rotation. Distal resection guide surface 146 is connected through a structure which allows it to be positioned relative to intramedullary or extramedullary rod 92 so that resection guide surface 146 can be oriented correctly relative to transition point 82 on the bone and oriented in varus/valgus to form the distal resection 100. Such structure in the embodiment shown in FIGS. 14-16 include a collet 148 and body 150. The collet includes indicia 152 to indicate desired varus/valgus orientation of the resection guide surface 146. Similar to the way in which distal resection instrumentation 102 may be used, the alternate distal resection guide surface 146 can be positioned in the superior/inferior direction relative to intramedullary rod 92 by sliding collet 148 on the rod. It can be adjusted in varus/valgus by using the indicia on the collet 148. As in the case of distal resection guide surface 104, the alternate distal resection guide surface 146 surface itself, without any markings or special physical distinctions, can serve as an index 154 for positioning of the alternate distal resection guide surface 146 so that the distal resection 100 passes through or near or relative as desired to the transition point 82. As with the case of distal resection guide surface 104, alternate distal resection guide surface 146 or other portion of alternate distal resection instrumentation 144 can contain indica (not shown) or other desired markings or features to serve as an index 154 for such proper alignment so that the distal resection 100 extends through, near or suitably relative to the transition point 82 and is correctly positioned in varus/valgus.

Implant sizing markings 156 can also be included, as shown in FIGS. 14-16 to allow this instrumentation 144, in a manner similar to anterior resection instrument 90 and/or distal resection instrumentation 102, to show or suggest to the surgeon what size of implant 10, and what size of transition resection guide 116, will be needed.

FIG. 17 shows distal portion 12 of femur 14 with what is left of anterior resection 84 after performing a transition resection 118 and chamfer resection 120 according to one embodiment of the invention. This view is taken before posterior resection 138 and posterior chamfer resection 142 have been performed.

FIG. 18 shows implant 10 installed on femur 14, with the knee in approximately 65 degrees of flexion. The posterior medial articulating surfaces 60 of implant 10 are articulating against tibial insert 40 of the medial compartment 52 of the knee, while natural bone of the lateral condyle 22 of the femur 14 and the tibial plateau 24, form the lateral compartment 42 of the knee 18.

FIGS. 19-25 show a resection guide 158 according to an alternate embodiment of the invention, which can resect bone so that implants 10 having one or move curved inner surfaces can be installed. Accordingly, an anterior resection 84, which may be flat or curved, can be formed using any desired resection device or guide, such as those discussed above, or milling apparatus with appropriately positioned guide. As in the devices discussed above, a bone transition point 82 which may be designated as desired, including the distal most point on the lateral portion of anterior resection 84. Upon designation of the transition point 82, guide 158 may be positioned on the distal portion of femur 12. In the structure shown in FIGS. 19-25, guide 158 features an anterior paddle 160 which may be substantially flat or curved as appropriate to correspond to anterior resection 84. The paddle or other portion of the guide 158 can also include a transition point index 162 for helping locate guide 158 relative to transition point 82. Transition point index 162 can be any desired physical or other marker or structure on guide 158 as desired. Also, helping position guide 158 relative to femur 14 is a collet 164 which is connected, preferably in adjustable relationship, to an intramedullary or extramedullary rod 166. Collet 164 could also be in the form of an adjustable structure with indicia as can be the case with resection guides discussed above, or a series of collets 164 each corresponding to a particular desired varus/valgus angle, may be employed, one of the collets 164 being selected for a particular application. Thus, guide 158 can be properly navigated and located relative to distal portion of femur 12 using the transition point 82 to help regulate the depth of the distal resection or distal surface to be formed by a milling device operating relative to guide 158, and proper navigation and location in varus/valgus and otherwise to cause guide 158 properly to guide milling or other resection devices to form curved surfaces, straight surfaces, or combinations, in proper orientation and position for proper kinematics of the reconstructed knee.

FIG. 20 shows guide 158 properly located on femur 14 to form a curved distal resection 112 and posterior resection 139, together with transition resection 118 (not shown in FIGS. 20-25, but similar in location and orientation to the transition resection 118 discussed in connection with resection guides disclosed above.) As shown in FIGS. 20-23, one or more medial condyle milling devices 168 can be guided by guide 158 to form distal resection 112 and posterior resection 139, both of which are curved and preferably meet in curved continuous fashion in the particular embodiment shown in FIGS. 20-23. Guide 158 can be constructed to use only one medial condyle milling device 168, multiple such devices, or as otherwise desired. Guide 158 can also be structured to allow the devices 168 to be positioned in order to rotate about a medial/lateral axis rather than as shown in FIGS. 20-23. A transition resection milling device 170 can be used to track within guide 158 to form the transition resection 118. FIGS. 24 and 25 show a shim 172 which may be coupled to guide 158 to help position guide 158 relative to medial condyle 20.

FIGS. 26-32 show a version of the guide 158 with a paddle 160 adapted to correspond to a curved anterior resection 84.

FIGS. 33-38 show a guide 174 according to another embodiment of the invention adapted to be navigated relative to the transition point 82 on a flat or curved anterior resection 84, and for forming a flat posterior resection 139 on medial condyle 20. Guide 174 can be navigated relative to the femur 14 using the transition point 82 on the femur 14 which has been designated as disclosed above, and relative to an intramedullary or extramedullary rod 166 using a collet 176. The collet 176 can be of the same sort as disclosed above in connection with guide 158. Once the guide 174 has been properly navigated and located, including if desired, like guide 158, being pinned to the bone in conventional fashion, the distal resection 112 can be formed using medial condyle milling devices in a fashion similar to that disclosed in connection with guide 158. Alternatively, surfaces of guide 174 can be used to guide a milling device whose rotational axis is in the medial lateral direction, as shown in FIG. 38 by way of example. Medial/lateral rotational milling device 176 can be wider than that shown in FIG. 38, if desired, and used with a guide 174 which uses slots or other desired structure to allow milling device 176 to rotate against bone on the medial condyle 20 to shape it appropriately, and for device 176 to be guided by and manipulated relative to guide 174. A transition milling device 170, not shown, may be used as in the guide 158, to form transition resection 118.

Guides 158 or 174 may be configured and structured as desired in order to guide one or more medial condyle milling devices 168 or 176 to form distal resection 112 and/or posterior resection 139 in a continuous curved fashion, with or without flat portions, or as otherwise desired. Guide 174 like guide 158 can be used in connection with flat or curved anterior resections 84 which resections may be formed using cutting blocks or milling guides.

FIGS. 39-49 show a resection guide 180 according to another alternate embodiment of the invention. Such a guide can incorporate functionality for forming not only the distal resection 112, transition resection 118 and posterior resection 139, but also anterior resection 84. The particular guide 180 shown in these figures is adapted to be positioned on a generally tubular collet 182. Collet 182 can be located and positioned on intramedullary or extramedullary rod 92 so that collet 182 and guide 180 may be properly positioned and then locked in place as desired relative to the rod 92. Any other collet can be used, whether or not adjustable or provided in a series to accommodate various angles of varus/varus. In the particular structure shown in these FIGS. 39-49, guide 180 can slide and then be locked in place relative to collet 180 in an anterior/posterior direction, as well as rotated and then locked into place relative to collet 182 to adjust guide 180 in a varus/valgus rotation as desired relative to femur 14. Accordingly, guide 180 can be positioned relative to intramedullary or extramedullary rod 92 in a varus/valgus and interior/exterior rotational direction, and in a superior/inferior and anterior/posterior translational direction, and then locked in place as desired in each of these rotations or translations. Guide 180 contains an anterior resection guide surface 184, a distal resection guide surface 186, a posterior resection guide surface 188, a transition resection guide surface 190, an anterior chamfer guide surface 192 and a posterior chamfer guide surface 194. A shim 196 can be used to help position guide 180 for proper distal and other resections. Shim 196 is shown in FIG. 43.

In use, intramedullary or extramedullary rod 92 is placed and the guide 190 of FIGS. 39-49 properly positioned relative to it on collet 182 to form an anterior resection 84 in accordance with the principles discussed in connection with the embodiment shown in FIGS. 5-8. Transition point 82 is then designated and a positioner 198 as shown in FIG. 43 can be connected to guide 190 to abut anterior resection 84 or otherwise referenced to it, and also reference positioner 198 and guide 180 relative to transition point 82 so that a distal resection 112 can be formed at proper depth to achieve proper flexion extension of the reconstructed knee. Positioner 198 can also contain the distal resection guide surface 186 for forming distal resection 112. Guide 180 and positioner 198 are shown properly navigated and located into place on the femur 14 for forming the distal resection 112. The other resections, including transition resection 118, posterior resection 139, anterior chamfer resection 120, posterior chamfer resection 142 can be formed using the respective guide surfaces 188, 190, 192, and 194. FIGS. 49 A and B show the resections formed on the bone using guide 180: anterior resection 84; distal resection 112, posterior resection 139, anterior chamfer resection 120 and posterior chamfer resection 142 and transition resection 118.

An implant such as that shown in FIGS. 1 and 2 can be installed on the femur 14 so resected.

The invention claimed is:

1. A method of preparing a distal femur for receipt of a femoral member, the femoral member including an anterior portion comprising an anterior medial articulating surface, an anterior lateral articulating surface, and an anterior patellofemoral portion, the anterior portion having a distal edge and a lateral margin; a posterior medial condylar portion comprising a posterior medial articulating surface; and a transition edge extending laterally from the distal edge of the anterior portion to the lateral margin of the anterior portion in an anterior direction, the method comprising:
placing a guide on the distal femur, the guide including a transition guide surface corresponding to the transition edge of the femoral member;
using the transition guide surface to locate on the femur the position of the transition edge of the femoral member; and
cutting bone to receive the transition edge of the femoral member.

2. The method of claim 1 further comprising using the guide to form an anterior resection of the distal femur for receiving the anterior portion of the femoral member.

3. The method of claim 1 further comprising using the guide to form a posterior resection of the distal femur for receiving the posterior medial condylar portion of the femoral member.

4. The method of claim 1 further comprising using the guide to form a distal resection of the distal femur.

5. The method of claim 1 further comprising using the guide to form a bore in the femur.

6. The method of claim 1 wherein the guide comprises:
an inner surface for receipt by a distal femur;
a posterior resection guide surface to guide resection of a posterior region of the distal femur for receiving the posterior medial condylar portion of the femoral member; and
an anterior resection guide surface to guide resection of an anterior region of the distal femur for receiving the anterior portion of the femoral member.

* * * * *